(12) United States Patent
Rivero et al.

(10) Patent No.: US 8,906,910 B2
(45) Date of Patent: Dec. 9, 2014

(54) IMIDAZOPYRIDINE DERIVATIVES AS PI3 KINASE

(71) Applicant: GlaxoSmithKline LLC, Philadelphia, PA (US)

(72) Inventors: Ralph A. Rivero, Collegeville, PA (US); Rosanna Tedesco, Collegeville, PA (US)

(73) Assignee: GlaxoSmithKline LLC, Wilmington, New Castle, DE (US)

( * ) Notice: Subject to any disclaimer, the term of this patent is extended or adjusted under 35 U.S.C. 154(b) by 0 days.

(21) Appl. No.: 14/357,227

(22) PCT Filed: Oct. 16, 2012

(86) PCT No.: PCT/US2012/060353
§ 371 (c)(1),
(2), (4) Date: May 9, 2014

(87) PCT Pub. No.: WO2013/095761
PCT Pub. Date: Jun. 27, 2013

(65) Prior Publication Data
US 2014/0323480 A1    Oct. 30, 2014

Related U.S. Application Data

(60) Provisional application No. 61/577,912, filed on Dec. 20, 2011.

(51) Int. Cl.
*A61K 31/5377* (2006.01)
*C07D 413/14* (2006.01)
*C07D 471/04* (2006.01)

(52) U.S. Cl.
CPC ............ *C07D 471/04* (2013.01); *C07D 413/14* (2013.01); *A61K 31/5377* (2013.01)
USPC ........................................ 514/234.2; 544/127

(58) Field of Classification Search
CPC . A61K 31/5377; C07D 471/04; C07D 413/14
USPC ........................................ 544/127; 514/234.2
See application file for complete search history.

(56) References Cited

U.S. PATENT DOCUMENTS

| | | | |
|---|---|---|---|
| 5,332,744 | A | 7/1994 | Chakravarty et al. |
| 6,627,624 | B1 | 9/2003 | Desimone et al. |
| 2008/0233127 | A1 | 9/2008 | Bursavich et al. |
| 2010/0305096 | A1 | 12/2010 | Castanedo et al. |
| 2011/0281865 | A1 | 11/2011 | Muthuppalaniappan et al. |

*Primary Examiner* — Rebecca Anderson
(74) *Attorney, Agent, or Firm* — J. Scott Young

(57) ABSTRACT

This invention relates to the use of imidizopyridine derivatives for the modulation, notably the inhibition of the activity or function of the phosphoinositide 3' OH kinase family (hereinafter PI3 kinases), suitably, PI3Kα, PI3Kδ, PI3Kβ, and/or PI3Kγ. Suitably, the present invention relates to the use of imidizopyridines in the treatment of one or more disease states selected from: autoimmune disorders, inflammatory diseases, cardiovascular diseases, neurodegenerative diseases, allergy, asthma, pancreatitis, multiorgan failure, kidney diseases, platelet aggregation, cancer, sperm motility, transplantation rejection, graft rejection and lung injuries. More suitably, the present invention relates to PI3Kβ selective imidizopyridine compounds for treating cancer.

7 Claims, No Drawings

IMIDAZOPYRIDINE DERIVATIVES AS PI3 KINASE

CROSS-REFERENCE TO RELATED APPLICATIONS

This application is filed pursuant to 35 USC 371 as a United States National Phase Application of International Patent Application Serial No. PCT/US2012/060353 filed on Oct. 16, 2012, which claims priority from 61/577,912 filed on Dec. 20, 2011 in the United States.

FIELD OF THE INVENTION

This invention relates to the use of imidizopyridine derivatives for the modulation, notably the inhibition of the activity or function of the phosphoinositide 3' OH kinase family (hereinafter PI3 kinases), suitably, PI3Kα, PI3Kδ, PI3Kβ, and/or PI3Kγ. Suitably, the present invention relates to the use of imidizopyridines in the treatment of one or more oncologic disorders. More suitably, the present invention relates to PI3Kβ selective imidizopyridine compounds for treating cancer.

BACKGROUND OF THE INVENTION

The phosphoinositide 3-kinase (PI3K) pathway is among the most commonly activated in human cancer and the importance in carcinogenesis is well established (Samuels Y and Ericson K. Oncogenic PI3K and its role in cancer. *Current Opinion in Oncology*, 2006; 18:77-82). Initiation of signaling begins with the phosphorylation of phosphatidylinositol-4,5-bisphosphate (PIP2) to produce phosphatidylinositol-3,4,5-P3 (PIP3). PIP3 is a critical second messenger which recruits proteins that contain pleckstrin homology domains to the cell membrane where they are activated. The most studied of these proteins is AKT which promotes cell survival, growth, and proliferation.

The PI3K family consists of 15 proteins that share sequence homology, particularly within their kinase domains, but have distinct substrate specificities and modes of regulation (Vivanco I and Sawyers C L. The phosphatidylinositol 3-kinase-AKT pathway in human cancer. *Nature Reviews Cancer*, 2002; 2:489-501). Class I PI3Ks are heterodimers consisting of a p110 catalytic subunit complexed to one of several regulatory subunits collectively referred to as p85 and have been the most extensively studied in the context of tumorgenesis. The class 1A PI3K catalytic subunits comprise the p110α, p110β, and p110δ isoforms, which associate with one of five different regulatory subunits encoded by three separate genes. A single class 1B PI3K catalytic isoform p110γ interacts with one of two associated regulatory subunits (Crabbe T, Welham M J, Ward S G, The PI3k inhibitor arsenal: choose your weapon *Trends in Biochem Sci,* 2007; 32:450-456). Class 1 PI3Ks are primarily responsible for phosphorylating the critical PIP2 signaling molecule.

The link between the PI3K pathway and cancer was confirmed by a study which identified somatic mutations in the PIK3CA gene encoding the p110α protein. Subsequently, mutations in PIK3CA have been identified in numerous cancers including colorectal, breast, glioblastomas ovarian and lung. In contrast to PIK3CA, no somatic mutations in the β isoform have been identified. However, in overexpression studies, the PI3Kβ isoform has been implicated as necessary for transformation induced by the loss or inactivation of the PTEN tumor suppressor both in vitro and in vivo (Torbett N E, Luna A, Knight Z A, et al., A chemical screen in diverse breast cancer cell lines reveals genetic enhancers and suppressors of sensitivity to PI3K isotype-selective inhibition. *Biochem J* 2008; 415:97-110; Zhao J J, Liu Z, Wang L, Shin E, Loda M F, Roberts T M, The oncogenic properties of mutant p110a and p110b phosphatidylinositol 3-kinases in human mammary epithelial cells. *Proc Natl Acad Sci USA* 2005; 102: 18443-8). Consistent with this finding, overexpression of the PIK3CB gene has been identified in some bladder, colon, glioblastomas and leukemias and siRNA mediated knockdown of p110β in glioblastoma cell lines results in suppression of tumor growth in vitro and in vivo (Pu P, Kang C, Zhang Z, et al., Downregulation of PIK3CB by siRNA suppresses malignant glioma cell growth in vitro and in vivo. *Technolo Cancer Res Treat* 2006; 5:271-280). More recent data using shRNA demonstrated that downregulation of p110β and not p110α resulted in PI3K pathway inactivation and subsequent inactivation of tumor cell growth in PTEN deficient cancers cells both in vitro and in vivo (Wee S, Wiederschain, Maira S-M, Loo A, Miller C, et al., PTEN-deficient cancers depend on PIK3CB. *Proc Natl Acad Sci* 2008; 105:13057-13062). Consistent with a role of PIK3CB signaling in PTEN null tumors, p110β was reported to be essential to the transformed phenotype in a PTEN-null prostate cancer model (Jia S, Liu Z, Zhang S, Liu P, Zhang L, et al., Essential roles of PI(3)K-p110b in cell growth, metabolism and tumorgenesis. *Nature* 2008; 10:1038).

Further, it has been reported that fibrogenesis, including systemic sclerosis (SSc), arthritis, nephropahty, liver cirrhosis, and some cancers, are related to PTEN deficiency and corresponding PI3K-Akt overexpression (Parapuram, S. K., et al., Loss of PTEN expression by dermal fibroblasts causes skin fibrosis. J. of Investigative Dermatology, advance online publication 9 Jun. 2011; doi: 10.1038/jid.2011.156). Taken together, these findings indicate PI3K p110β as a promising target for cancer and other syndromes related to PTEN loss (Hollander, M. Christine; Blumenthal, Gideon M.; Dennis, Phillip P.; PTEN loss in the continuum of common cancers, rare syndromes and mouse models. *Nature Reviews/Cancer* 2011; 11: 289-301). It is therefore desirable to create a potent, selective inhibitor of PI3K-β.

SUMMARY OF THE INVENTION

This invention relates to novel compounds of formula (I):

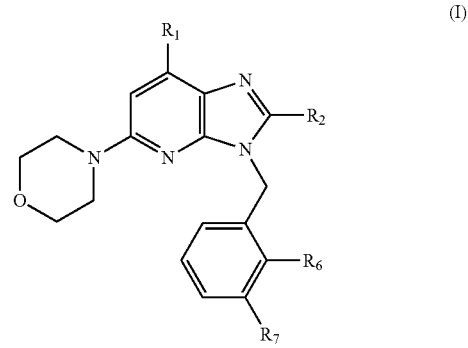

wherein
R1 is selected from H, —OH, and —C(O)OH;
R2 is selected from H, and $C_{1-3}$alkyl; and
each of R6 and R7 is independently selected from $C_{1-3}$alkyl, halogen, and —$CF_3$, or R6 and R7 combine with the ring to which they are attached to form napththal;
or a pharmaceutically acceptable salt thereof.

In another aspect of the present invention, there is provided a method of treating a susceptible neoplasm in a mammal in need thereof, comprising administering to the mammal a therapeutically effective amount of a compound of formula (I) (including any particular sub-generic formula described herein) or a pharmaceutically acceptable salt thereof.

In another aspect of the present invention, there is provided a compound of formula (I), (including any particular sub-generic formula described herein) or a pharmaceutically acceptable salt thereof for use in therapy.

In another aspect, there is provided a compound of formula (I) (including any particular sub-generic formula described herein) or a pharmaceutically acceptable salt thereof for use in the treatment of a susceptible neoplasm in a mammal in need thereof.

In a another aspect of the present invention, there is provided the use of a compound of formula (I) (including any particular sub-generic formula described herein) or a pharmaceutically acceptable salt thereof, in the preparation of a medicament for use in the treatment of a susceptible neoplasm in a mammal in need thereof.

In another aspect of the present invention, there is provided a pharmaceutical composition comprising a compound of formula (I) (including any particular sub-generic formula described herein) or a pharmaceutically acceptable salt thereof for use in the treatment of a susceptible neoplasm in a mammal in need thereof.

DETAILED DESCRIPTION OF THE INVENTION

This invention is directed to compounds of Formula (I).

According to another embodiment, the invention includes compounds of formula (I)(A):

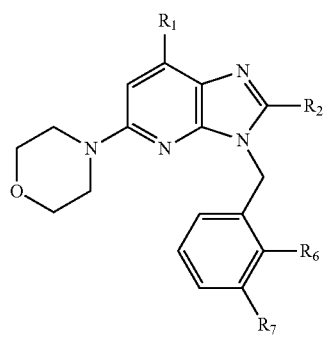

(I)(A)

wherein
R1 is selected from H, —OH, and —C(O)OH;
R2 is selected from H, and $C_{1-3}$alkyl; and
each of R6 and R7 is independently selected from $C_{1-3}$alkyl, halogen, and —$CF_3$;
or a pharmaceutically acceptable salt thereof.

According to another embodiment, the invention includes compounds of formula (I)(A) as defined above wherein R2 is methyl.

According to another embodiment, the invention includes the compounds of Formula (I)(B)

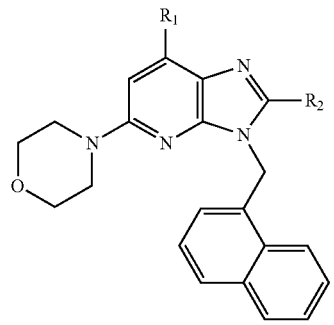

(I)(B)

wherein
R1 is selected from H, —OH, and —C(O)OH; and
R2 is selected from H, and $C_{1-3}$alkyl;
or a pharmaceutically acceptable salt thereof.

According to another embodiment, the invention includes compounds:
3-(2-methyl-3-(trifluoromethyl)benzyl)-5-morpholino-3H-imidazo[4,5-b]pyridin-7-ol;
5-morpholino-3-(naphthalen-1-ylmethyl)-3H-imidazo[4,5-b]pyridin-7-ol;
2-methyl-3-(2-methyl-3-(trifluoromethyl)benzyl)-5-morpholino-3H-imidazo[4,5-b]pyridine-7-carboxylic acid;
3-(2,3-dichlorobenzyl)-2-methyl-5-morpholino-3H-imidazo[4,5-b]pyridine-7-carboxylic acid;
3-(3-chloro-2-methylbenzyl)-2-methyl-5-morpholino-3H-imidazo[4,5-b]pyridine-7-carboxylic acid;
2-methyl-5-morpholino-3-(naphthalen-1-ylmethyl)-3H-imidazo[4,5-b]pyridine-7-carboxylic acid;
4-(2-methyl-3-(naphthalen-1-ylmethyl)-3H-imidazo[4,5-b]pyridin-5-yl)morpholine; and
4-(3-(2,3-dichlorobenzyl)-2-methyl-3H-imidazo[4,5-b]pyridin-5-yl)morpholine.

DEFINITIONS

By the term "aryl" as used herein, unless otherwise defined, is meant aromatic, hydrocarbon, ring system. The ring system may be monocyclic or fused polycyclic (e.g. bicyclic, tricyclic, etc.). In various embodiments, the monocyclic aryl ring is C5-C10, or C5-C7, or C5-C6, where these carbon numbers refer to the number of carbon atoms that form the ring system. A C6 ring system, i.e. a phenyl ring is a suitable aryl group. In various embodiments, the polycyclic ring is a bicyclic aryl group, where suitable bicyclic aryl groups are C8-C12, or C9-C10. A naphthyl ring, which has 10 carbon atoms, is a suitable polycyclic aryl group.

By the term "heteroaryl" as used herein, unless otherwise defined, is meant an aromatic ring system containing carbon(s) and at least one heteroatom. Heteroaryl may be monocyclic or polycyclic. A monocyclic heteroaryl group may have 1 to 4 heteroatoms in the ring, while a polycyclic heteroaryl may contain 1 to 10 hetero atoms. A polycyclic heteroaryl ring may contain fused, spiro or bridged ring junctions, for example, bicyclic heteroaryl is a polycyclic heteroaryl. Bicyclic heteroaryl rings may contain from 8 to 12 member atoms. Monocyclic heteroaryl rings may contain from 5 to 8 member atoms (carbons and heteroatoms). Exemplary heteroaryl groups include: benzofuran, benzothiene, benzothiophene, furan, imidazole, indole, isothiazole, oxazole, pyrazine, pyrazole, pyridazine, pyridine, pyrimidine, pyrrole, quinoline, isoquinoline, quinazoline, quinoxaline, thiazole, and thiophene. According to an alternative embodiment, heteroaryls may be substituted with one to three alkyl groups.

By the term "alkoxy" as used herein is meant —O(alkyl) including —OCH$_3$, —OCH$_2$CH$_3$ and —OC(CH$_3$)$_3$ where alkyl is as described herein.

By the term "heteroatom" as used herein is meant oxygen, nitrogen or sulfur.

By the term "halogen" as used herein is meant a substituent selected from bromide, iodide, chloride and fluoride.

By the term "alkyl" and derivatives thereof and in all carbon chains as used herein, including alkyl chains defined by the term "—(CH$_2$)$_n$—", "—(CH$_2$)$_m$—" and the like, is meant a linear or branched, saturated or unsaturated hydrocarbon chain, and unless otherwise defined, the carbon chain will contain from 1 to 12 carbon atoms.

By the term "co-administering" and derivatives thereof as used herein is meant either simultaneous administration or any manner of separate sequential administration of a PI3 kinase inhibiting compound, as described herein, and a further active ingredient or ingredients. The term further active ingredient or ingredients, as used herein, includes any compound or therapeutic agent known to or that demonstrates advantageous properties when administered to a patient in need of treatment. Suitably, if the administration is not simultaneous, the compounds are administered in a close time proximity to each other. Furthermore, it does not matter if the compounds are administered in the same dosage form, e.g. one compound may be administered topically and another compound may be administered orally.

The term "compound" as used herein includes all isomers of the compound. Examples of such isomers include: enantiomers, tautomers, rotamers.

In formulas where a "dotted" bond is drawn between two atoms, it is meant that such bond can be either single or double bond. A ring system containing such bonds can be aromatic or non-aromatic.

Certain compounds described herein may contain one or more chiral atoms, or may otherwise be capable of existing as two enantiomers, or two or more diastereoisomers. Accordingly, the compounds of this invention include mixtures of enantiomers/diastereoisomers as well as purified enantiomers/diastereoisomers or enantiomerically/diastereoisomerically enriched mixtures. Also included within the scope of the invention are the individual isomers of the compounds represented by Formula (I) above as well as any wholly or partially equilibrated mixtures thereof. The present invention also covers the individual isomers of the compounds represented by the formulas above as mixtures with isomers thereof in which one or more chiral centers are inverted. The present invention also includes isotopomers of the compounds of Formula (I). Examples of such isotopomers include but not limited to compounds with one of more deuterium atoms.

Compounds of Formula (I) are included in the pharmaceutical compositions of the invention. Where a —COOH or —OH group is present, pharmaceutically acceptable esters can be employed, for example methyl, ethyl, pivaloyloxymethyl, and the like for —COOH, and acetate maleate and the like for —OH, and those esters known in the art for modifying solubility or hydrolysis characteristics, for use as sustained release or prodrug formulations.

It will be appreciated by those skilled in the art that the compounds of formula (I) may be utilized as a pharmaceutically acceptable salt version thereof. The pharmaceutically acceptable salts of the compounds of formula (I) include conventional salts formed from pharmaceutically acceptable (i.e., non-toxic) inorganic or organic acids or bases as well as quaternary ammonium salts. Representative salts include the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, ethanol amine, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate (methanesulfonate), methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate (methylbenzenesulfonate), triethiodide, trimethylammonium and valerate. Other salts, such as oxalic and trifluoroacetic, which are not themselves pharmaceutically acceptable, may be useful in the preparation of salts useful as intermediates in obtaining compounds of this invention and these form a further aspect of the invention. In one embodiment, the compound of formula (I) is in the form of the free base. Certain salt versions of the compounds may be solvates, particularly hydrates. In one embodiment, the compound of formula (I) or a pharmaceutically acceptable salt thereof is in the form of a mono-, di-, tri- or hemi-hydrate.

It has now been found that compounds of the present invention are inhibitors of the Phosphatoinositides 3-kinases (PI3Ks). When the phosphatoinositides 3-kinase (PI3K) enzyme is inhibited by a compound of the present invention, PI3K is unable to exert its enzymatic, biological and/or pharmacological effects. The compounds of the present invention are therefore useful in the treatment of autoimmune disorders, inflammatory diseases, cardiovascular diseases, neurodegenerative diseases, allergy, asthma, pancreatitis, multiorgan failure, kidney diseases, platelet aggregation, cancer, sperm motility, transplantation rejection, graft rejection and lung injuries.

Compounds according to Formula (I) are suitable for the modulation, notably the inhibition of the activity of phosphatoinositides 3-kinases (PI3K) and, more particularly, selective inhibitors of the beta isoform of phosphatoinositides 3-kinase (PI3Kβ). Therefore the compounds of the present invention are also useful for the treatment of disorders which are mediated by PI3Ks. Said treatment involves the modulation—notably the inhibition or the down regulation—of the phosphatoinositides 3-kinases.

Because the pharmaceutically active compounds of the present invention are active as PI3 kinase inhibitors, particularly the compounds that inhibit PI3Kβ, either selectively or in conjunction with one or more of PI3Kδ, PI3Kα, and/or PI3Kγ, they exhibit therapeutic utility in treatment of susceptible neoplasms, particularly those neoplasms that exhibit a PTEN deficiency.

As used herein, the phrase "PTEN deficient" or "PTEN deficiency" shall describe tumors with deficiencies of the tumor suppressor function of PTEN (Phosphatase and Tensin Homolog). Such deficiency includes mutation in the PTEN gene, reduction or absence of PTEN proteins when compared to PTEN wild-type, or mutation or absence of other genes that cause suppression of PTEN function.

As used herein, the term "treatment" or "treating" in the context of therapeutic methods, refers to alleviating the specified condition, eliminating or reducing the symptoms of the condition, slowing or eliminating the progression, invasion, or metastatic spread of the condition and preventing or delaying the reoccurrence of the condition in a previously afflicted subject. The present invention further provides use of the compounds of the invention for the preparation of a medicament for the treatment of several conditions in a mammal (e.g., human) in need thereof.

"Susceptible neoplasm" as used herein refers to neoplasms which are susceptible to treatment by a kinase inhibitor and particularly neoplasms that are susceptible to treatment by a PI3Kβ inhibitor. Neoplasms which have been associated with inappropriate activity of the PTEN phosphatase and particularly neoplasms which are exhibit mutation of PTEN, or mutation of an upstream activator of PI3Kβ kinase or overexpression of an upstream activator of PI3Kβ kinase, and are therefore susceptible to treatment with an PI3Kβ inhibitor are known in the art, and include both primary and metastatic tumors and cancers. According to one embodiment, description of the treatment of a susceptible neoplasm may be used interchangeably with description of the treatment of a cancer.

According to one embodiment, "susceptible neoplasms" includes, but are not limited to PTEN-deficient neoplasms listed as follows:
brain (gliomas),
glioblastomas,
leukemias,
Bannayan-Zonana syndrome,
Cowden disease,
Lhermitte-Duclos disease,
breast cancer,
inflammatory breast cancer,
colorectal cancer
Wilm's tumor,
Ewing's sarcoma,
Rhabdomyosarcoma,
ependymoma,
medulloblastoma,
colon cancer,
head and neck cancer,
kidney cancer,
lung cancer,
liver cancer,
melanoma,
squamous cell carcinoma,
ovarian cancer,
pancreatic cancer,
prostate cancer,
sarcoma cancer,
osteosarcoma,
giant cell tumor of bone,
thyroid cancer,
lymphoblastic T cell leukemia,
chronic myelogenous leukemia,
chronic lymphocytic leukemia,
hairy-cell leukemia,
acute lymphoblastic leukemia,
acute myelogenous leukemia,
chronic neutrophilic leukemia,
acute lymphoblastic T cell leukemia,
Plasmacytoma,
Immunoblastic large cell leukemia,
Mantle cell leukemia,
Multiple myeloma,
Megakaryoblastic leukemia,
multiple myeloma,
Acute megakaryocytic leukemia,
promyelocytic leukemia,
Erythroleukemia,
malignant lymphoma,
hodgkins lymphoma,
non-hodgkins lymphoma,
lymphoblastic T cell lymphoma,
Burkitt's lymphoma,
follicular lymphoma,
neuroblastoma,
bladder cancer,
urothelial cancer,
vulval cancer,
cervical cancer,
endometrial cancer,
renal cancer,
mesothelioma,
esophageal cancer,
salivary gland cancer,
hepatocellular cancer,
gastric cancer,
nasopharangeal cancer,
buccal cancer,
cancer of the mouth,
GIST (gastrointestinal stromal tumor),
and testicular cancer.

According to an alternative embodiment, the term "susceptible neoplasm" includes and is limited to hormone refractory prostate cancer, non-small-cell lung cancer, endometrial cancer, gastric cancer, melanoma, head and neck cancer, breast cancer, including trip-negative breast cancer, and glioma. PTEN deficiency has been correlated to such cancers as demonstrated in a number of published resources, e.g. Am J Clin Pathol. 2009 February; 131(2):257-63 (glioblastoma), J Clin Neurosci. 2010 December; 17(12): 1543-7 (glioblastoma), Nat. Genet. 2009 May; 41(5):619-24 (prostate cancer), Br J Cancer. 2008 Oct. 21; 99(8):1296-301 (prostate cancer), Int J Cancer. 2007 Mar. 15; 120(6):1284-92 (prostate cancer), J Invest Dermatol. 2006 January; 126(1):154-60 (melanoma), J Clin Oncol. 2006 Jan. 10; 24(2):288-95 (melanoma), Am J Clin Pathol. 2005 October; 124(4):528-36 (melanoma), Int J Oncol. 2009 April; 34(4):983-93 (breast cancer), Epigenetics. 2011 May 1; 6(5):638-49 (breast cancer), Gynecol Oncol. 2009 February; 112(2):307-13 (ovarian cancer), Mod Pathol. 2010 October; 23(10):1316-24 (ovarian cancer), J Pathol. 2010 February; 220(3):392-400 (ovarian cancer), Lung. 2009 March-April; 187(2):104-9 (lung cancer), Anticancer Res. 2007 January-February; 27(1B):575-81 (lung cancer), Am J. Surg. 2008 June; 195(6):719-25 (colon cancer), J Clin Oncol. 2009 Dec. 10; 27(35):5924-30 (colon cancer), Gynecol Oncol. 2004 June; 93(3):621-7 (cervical cancer), and J Oral Pathol Med. 2002 August; 31(7):379-84 (head and neck cancer).

In another aspect of the present invention, there is provided a method of treating a susceptible neoplasm in a mammal in need thereof, comprising administering to the mammal a therapeutically effective amount of a compound of formula (I) (including any particular sub-generic formula described herein) or a pharmaceutically acceptable salt thereof.

In another aspect of the present invention, there is provided a method of treating fibrosis in a mammal in need thereof, comprising administering to the mammal a therapeutically effective amount of a compound of formula (I) (including any particular sub-generic formula described herein) or a pharmaceutically acceptable salt thereof. Fibrosis includes, alternatively or collectively, systemic sclerosis (SSc), arthritis, nephropahty, and liver cirrhosis.

In another aspect of the present invention, there is provided a method of treating hormone refractory prostate cancer in a mammal in need thereof, comprising administering to the mammal a therapeutically effective amount of a compound of formula (I) (including any particular sub-generic formula described herein) or a pharmaceutically acceptable salt thereof.

In another aspect of the present invention, there is provided a method of treating non-small-cell lung cancer in a mammal in need thereof, comprising administering to the mammal a therapeutically effective amount of a compound of formula (I) (including any particular sub-generic formula described herein) or a pharmaceutically acceptable salt thereof.

In another aspect of the present invention, there is provided a method of treating endometrial cancer in a mammal in need thereof, comprising administering to the mammal a therapeutically effective amount of a compound of formula (I) (including any particular sub-generic formula described herein) or a pharmaceutically acceptable salt thereof.

In another aspect of the present invention, there is provided a method of treating gastric cancer in a mammal in need thereof, comprising administering to the mammal a therapeutically effective amount of a compound of formula (I) (including any particular sub-generic formula described herein) or a pharmaceutically acceptable salt thereof.

In another aspect of the present invention, there is provided a method of treating melanoma in a mammal in need thereof, comprising administering to the mammal a therapeutically effective amount of a compound of formula (I) (including any particular sub-generic formula described herein) or a pharmaceutically acceptable salt thereof.

In another aspect of the present invention, there is provided a method of treating head and neck cancer in a mammal in need thereof, comprising administering to the mammal a therapeutically effective amount of a compound of formula (I) (including any particular sub-generic formula described herein) or a pharmaceutically acceptable salt thereof.

In another aspect of the present invention, there is provided a method of treating trip-negative breast cancer in a mammal in need thereof, comprising administering to the mammal a therapeutically effective amount of a compound of formula (I) (including any particular sub-generic formula described herein) or a pharmaceutically acceptable salt thereof.

In another aspect of the present invention, there is provided a method of treating glioma in a mammal in need thereof, comprising administering to the mammal a therapeutically effective amount of a compound of formula (I) (including any particular sub-generic formula described herein) or a pharmaceutically acceptable salt thereof.

In another aspect of the present invention, there is provided a compound of formula (I), (including any particular sub-generic formula described herein) or a pharmaceutically acceptable salt thereof for use in therapy.

In another aspect, there is provided a compound of formula (I) (including any particular sub-generic formula described herein) or a pharmaceutically acceptable salt thereof for use in the treatment of a susceptible neoplasm in a mammal in need thereof.

In a another aspect of the present invention, there is provided the use of a compound of formula (I) (including any particular sub-generic formula described herein) or a pharmaceutically acceptable salt thereof, in the preparation of a medicament for use in the treatment of a susceptible neoplasm in a mammal in need thereof.

In another aspect of the present invention, there is provided a pharmaceutical composition comprising a compound of formula (I) (including any particular sub-generic formula described herein) or a pharmaceutically acceptable salt thereof for use in the treatment of a susceptible neoplasm in a mammal in need thereof.

When a compound of Formula (I) is administered for the treatment of cancer, the term "co-administering" and derivatives thereof as used herein is meant either simultaneous administration or any manner of separate sequential administration of a PI3 kinase inhibiting compound, as described herein, and a further active ingredient or ingredients, known to be useful in the treatment of cancer, including chemotherapy and radiation treatment. The term further active ingredient or ingredients, as used herein, includes any compound or therapeutic agent known to or that demonstrates advantageous properties when administered to a patient in need of treatment for cancer. Preferably, if the administration is not simultaneous, the compounds are administered in a close time proximity to each other. Furthermore, it does not matter if the compounds are administered in the same dosage form, e.g. one compound may be administered topically and another compound may be administered orally.

Typically, any anti-neoplastic agent that has activity versus a susceptible tumor being treated may be co-administered in the treatment of cancer in the present invention. Examples of such agents can be found in Cancer Principles and Practice f Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracycline, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; and cell cycle signaling inhibitors.

Examples of a further active ingredient or ingredients for use in combination or co-administered with the present PI3 kinase inhibiting compounds are chemotherapeutic agents.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the $G_2$/M phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)-N-benzoyl-3-phenylisoserine; is a natural diterpene product isolated from the Pacific yew tree *Taxus brevifolia* and is commercially available as an injectable solution TAXOL®. It is a member of the taxane family of terpenes. It was first isolated in 1971 by Wani et al. J. Am. Chem., Soc., 93:2325. 1971), who characterized its structure by chemical and X-ray crystallographic methods. One mechanism for its activity relates to paclitaxel's capacity to bind tubulin, thereby inhibiting cancer cell growth. Schiff et al., Proc. Natl. Acad, Sci. USA, 77:1561-1565 (1980); Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann. Intem, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine, N-tert-butyl ester, 13-ester with 5β-20-epoxy-1,2α,4,7β,10β,13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine [R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine [1,1-cyclobutane-dicarboxylate(2-)-O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxy, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also know as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas. Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leucopenia tends to be more severe than thrombocytopenia.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leucopenia and thrombocytopenia.

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mercaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2(1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leucopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leucopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leucopenia, thrombocytopenia, and anemia, is the most common dose limiting side effect of gemcitabine administration.

Methotrexate, N-[4[[(2,4-diamino-6-pteridinyl)methyl]methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leucopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino)carbonyloxy]-1H-pyrano[3',4',6,7]indolizino[1,2-b]quinoline-3,14(4H,12H)-dione hydrochloride, is commercially available as the injectable solution CAMPTOSAR®.

Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Also of interest, is the camptothecin derivative of formula A following, currently under development, including the racemic mixture (R,S) form as well as the R and S enantiomers:

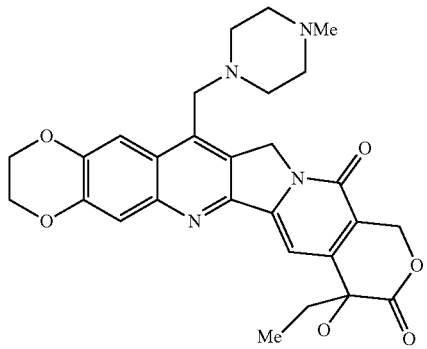

A known by the chemical name "7-(4-methylpiperazino-methylene)-10,11-ethylenedioxy-20(R,S)-camptothecin (racemic mixture) or "7-(4-methylpiperazino-methylene)-10,11-ethylenedioxy-20(R)-camptothecin (R enantiomer) or "7-(4-methylpiperazino-methylene)-10,11-ethylenedioxy-20(S)-camptothecin (S enantiomer). Such compound as well as related compounds are described, including methods of making, in U.S. Pat. Nos. 6,063,923; 5,342,947; 5,559,235; 5,491,237 and pending U.S. patent application Ser. No. 08/977,217 filed Nov. 24, 1997.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagonists such as goserelin acetate and luprolide.

Signal transduction pathway inhibitors are those inhibitors, which block or inhibit a chemical process which evokes an intracellular change. As used herein this change is cell proliferation or differentiation. Signal tranduction inhibitors useful in the present invention include inhibitors of receptor tyrosine kinases, non-receptor tyrosine kinases, SH2/SH3domain blockers, serine/threonine kinases, phosphotidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by overexpression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C., Exp. Opin. Ther. Patents (2000) 10(6):803-818; Shawver et al DDT Vol 2, No. 2 Feb. 1997; and Lofts, F. J. et al, "Growth factor receptors as targets", New Molecular Targets for Cancer Chemotherapy, ed. Workman, Paul and Kerr, David, CRC press 1994, London.

Tyrosine kinases, which are not growth factor receptor kinases are termed non-receptor tyrosine kinases. Non-receptor tyrosine kinases useful in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S, and Corey, S. J., (1999) Journal of Hematotherapy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta) IkB kinase family (IKKa, IKKb), PKB family kinases, AKT kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; and Martinez-Iacaci, L., et al, Int. J. Cancer (2000), 88(1), 44-52.

Inhibitors of Phosphotidyl inositol-3 Kinase family members including blockers of PI3-kinase, ATM, DNA-PK, and Ku are also useful in the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also useful in the present invention are Myo-inositol signaling inhibitors such as phospholipase C blockers and Myo-inositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and BioChem. Biophys. Acta, (19899) 1423(3):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al, Monoclonal Antibody Therapy for Solid Tumors, Cancer Treat. Rev., (2000), 26(4), 269-286); Herceptin® erbB2 antibody (see Tyrosine Kinase Signalling in Breast cancer:erbB Family Receptor Tyrosine Kinases, Breast cancer Res., 2000, 2(3), 176-183); and 2CB VEGFR2 specific antibody (see Brekken, R. A. et al, Selective Inhibition of VEGFR2 Activity by a monoclonal Anti-VEGF antibody blocks tumor growth in mice, Cancer Res. (2000) 60, 5117-5124).

Non-receptor kinase angiogenesis inhibitors may also find use in the present invention. Inhibitors of angiogenesis related VEGFR and TIE2 are discussed above in regard to signal transduction inhibitors (both receptors are receptor tyrosine kinases). Accordingly, non-receptor tyrosine kinase inhibitors may be used in combination with the inhibitors of the present invention. For example, anti-VEGF antibodies, which do not recognize VEGFR (the receptor tyrosine kinase), but bind to the ligand; small molecule inhibitors of integrin (alpha$_v$ beta$_3$) that will inhibit angiogenesis; endostatin and angiostatin (non-RTK) may also prove useful in combination with the disclosed family inhibitors. (See Bruns C J et al (2000), Cancer Res., 60: 2926-2935; Schreiber A B, Winkler M E, and Derynck R. (1986), Science, 232: 1250-1253; Yen L et al. (2000), Oncogene 19: 3460-3469).

Agents used in immunotherapeutic regimens may also be useful in combination with the compounds of formula (I). There are a number of immunologic strategies to generate an immune response against erbB2 or EGFR. These strategies are generally in the realm of tumor vaccinations. The efficacy of immunologic approaches may be greatly enhanced through combined inhibition of erbB2/EGFR signaling pathways using a small molecule inhibitor. Discussion of the immunologic/tumor vaccine approach against erbB2/EGFR are found in Reilly R T et al. (2000), Cancer Res. 60: 3569-3576; and Chen Y, Hu D, Eling D J, Robbins J, and Kipps T J. (1998), Cancer Res. 58: 1965-1971.

Agents used in proapoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., mcl-1). Therefore, strategies designed to downregulate the expression of bcl-2 in tumors have demonstrated clinical benefit and are now in Phase II/III trials, namely Genta's G3139 bcl-2 antisense oligonucleotide. Such proapoptotic strategies using the antisense oligonucleotide strategy for bcl-2 are discussed in Water J S et al. (2000), J. Clin. Oncol. 18: 1812-1823; and Kitada S et al. (1994), Antisense Res. Dev. 4: 71-79.

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin. Ther. Patents (2000) 10(2):215-230.

In one embodiment, the cancer treatment method of the claimed invention includes the co-administration a compound of formula I and/or a pharmaceutically acceptable salt, hydrate, solvate or pro-drug thereof and at least one antineoplastic agent, such as one selected from the group consisting of anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, and cell cycle signaling inhibitors.

The pharmaceutically active compounds of the present invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the presently invented pharmaceutically active compounds in a pharmaceutical dosage unit as described above will be an efficacious, nontoxic quantity preferably selected from the range of 0.001-100 mg/kg of active compound, preferably 0.001-50 mg/kg. When treating a human patient in need of a PI3K inhibitor, the selected dose is administered preferably from 1-6 times daily, orally or parenterally. Preferred forms of parenteral administration include topically, rectally, transdermally, by injection and continuously by infusion. Oral dosage units for human administration preferably contain from 0.05 to 3500 mg of active compound. According to one embodiment, the oral dosage for human administration contains 100 to 1000 mg per day. Oral administration, which uses lower dosages is preferred. Parenteral administration, at high dosages, however, also can be used when safe and convenient for the patient.

Optimal dosages to be administered may be readily determined by those skilled in the art, and will vary with the particular PI3 kinase inhibitor in use, the strength of the preparation, the mode of administration, and the advancement of the disease condition. Additional factors depending on the particular patient being treated will result in a need to adjust dosages, including patient age, weight, diet, and time of administration. Exemplary dosages include oral formulations equivalent to 10 mg, 25 mg, and 100 mg of the compound of formula (I), to be administered alone, in multiples, or in combination.

The method of this invention of inducing PI3 kinase inhibitory activity in mammals, including humans, comprises administering to a subject in need of such activity an effective PI3 kinase modulating/inhibiting amount of a pharmaceutically active compound of the present invention.

The invention also provides for the use of a compound of Formula (I) in the manufacture of a medicament for use as a PI3 kinase inhibitor.

The invention also provides for the use of a compound of Formula (I) in the manufacture of a medicament for use in therapy.

The invention also provides for the use of a compound of Formula (I) in the manufacture of a medicament for use in treating autoimmune disorders, inflammatory diseases, cardiovascular diseases, neurodegenerative diseases, allergy, asthma, pancreatitis, multiorgan failure, kidney diseases, platelet aggregation, cancer, sperm motility, transplantation rejection, graft rejection and lung injuries.

The invention also provides for a pharmaceutical composition for use as a PI3 inhibitor which comprises a compound of Formula (I) and a pharmaceutically acceptable carrier.

The invention also provides for a pharmaceutical composition for use in the treatment of autoimmune disorders, inflammatory diseases, cardiovascular diseases, neurodegenerative diseases, allergy, asthma, pancreatitis, multiorgan failure, kidney diseases, platelet aggregation, cancer, sperm motility, transplantation rejection, graft rejection and lung injuries, which comprises a compound of Formula (I) and a pharmaceutically acceptable carrier.

In addition, the pharmaceutically active compounds of the present invention can be co-administered with further active ingredients, including compounds known to have utility when used in combination with a PI3 kinase inhibitor.

Without further elaboration, it is believed that one skilled in the art can, using the preceding description, utilize the present invention to its fullest extent. The following examples are, therefore, to be construed as merely illustrative and not a limitation of the scope of the present invention in any way.

Experimental Procedures

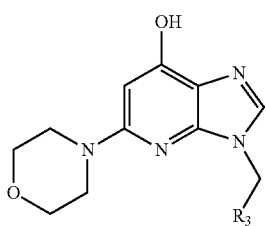

Formula I

Compounds of Formula (I) may be prepared using the general scheme I, as described below.

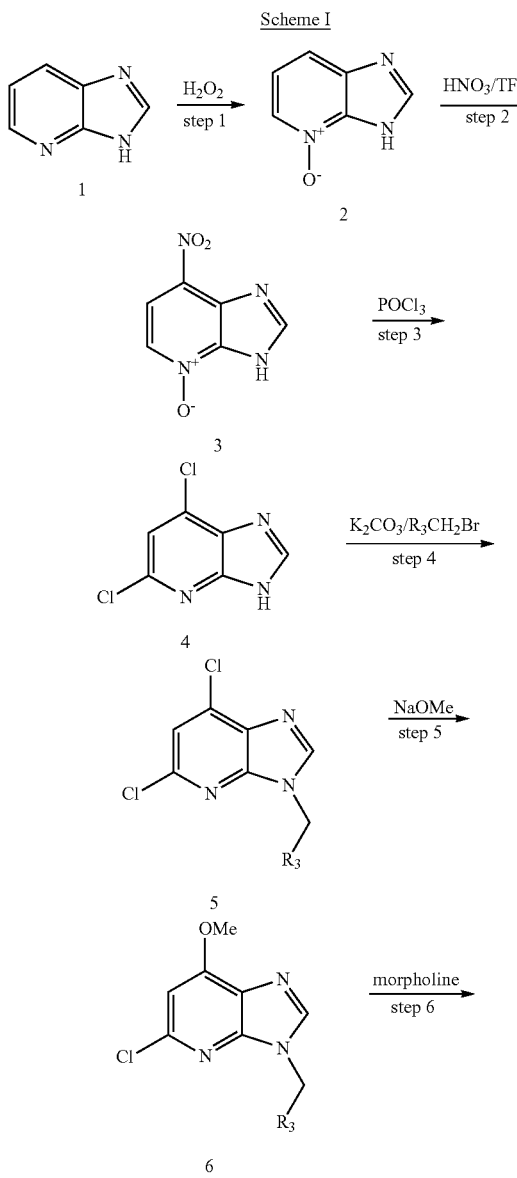

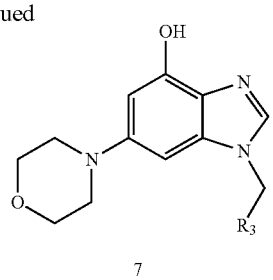

Hydrogen peroxide oxidation of 1H-imidazo[4,5-b]pyridine in acetic acid at elevated temperatures can provide the desired N-oxide (2) which can be nitrated with nitric acid in TFA to provide nitro-analog 3. Treatment of 3 with POCl₃ can then produce dichloro analog 4 that can be alkylated with a variety of alkyl halides in the presence of an appropriate base such as K₂CO₃ or Cs₂CO₃ in a polar aprotic solvent like DMF to provide 5. Treatment of 5 with morpholine at elevated temperatures in a microwave reactor results in demethylation and displacement of the chloride by morpholine to produce final compounds 7.

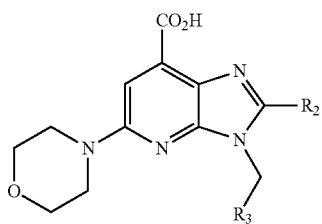

Formula II

Compounds of Formula (II) may be prepared using the general scheme II, as described below.

Scheme II

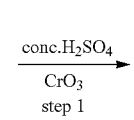

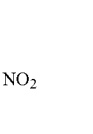

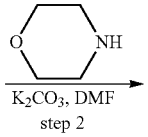

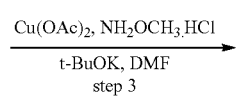

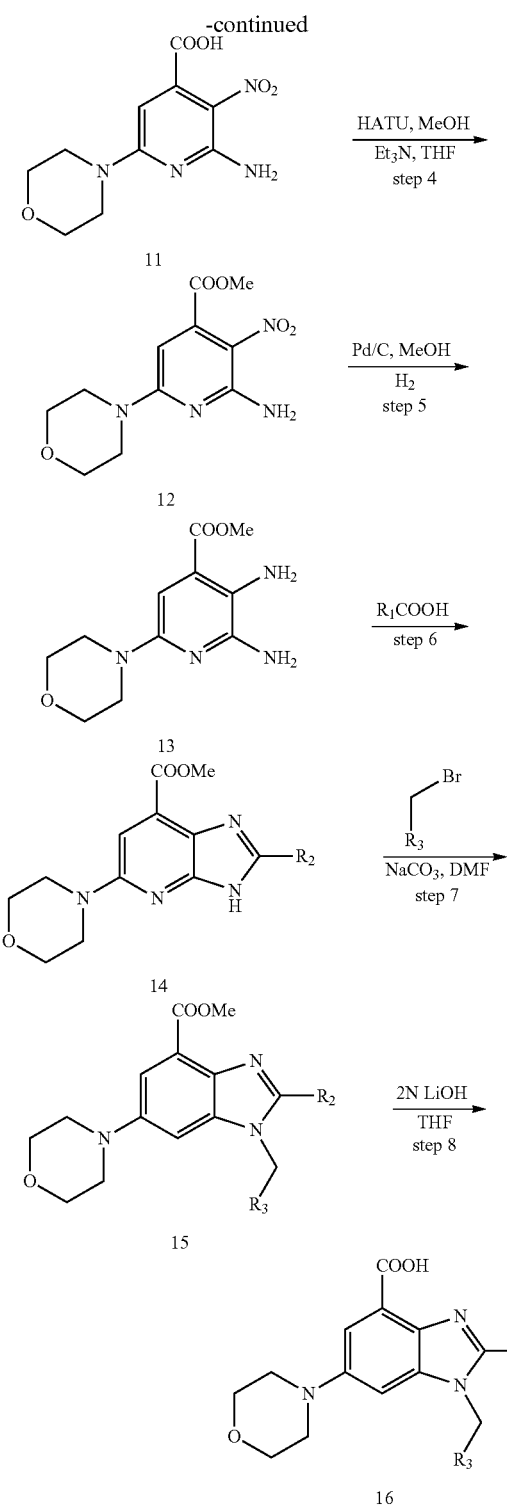

imidazopyridine (14) formation by heating with a carboxylic acid. Alkylation of imidazopyridine 14 can be carried out with an alkyl bromide in the presence of suitable base, such as $Na_2CO_3$, in a polar aprotic solvent like DMF, to provide 15. Ester hydrolysis under standard conditions provides final products 16.

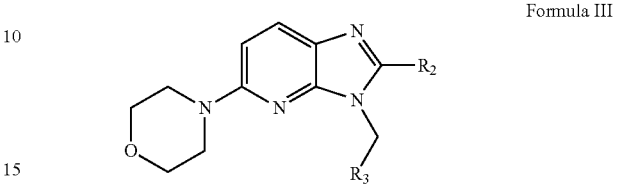

Formula III

Compounds of Formula (III) may be prepared using the general scheme III, as described below.

Scheme III

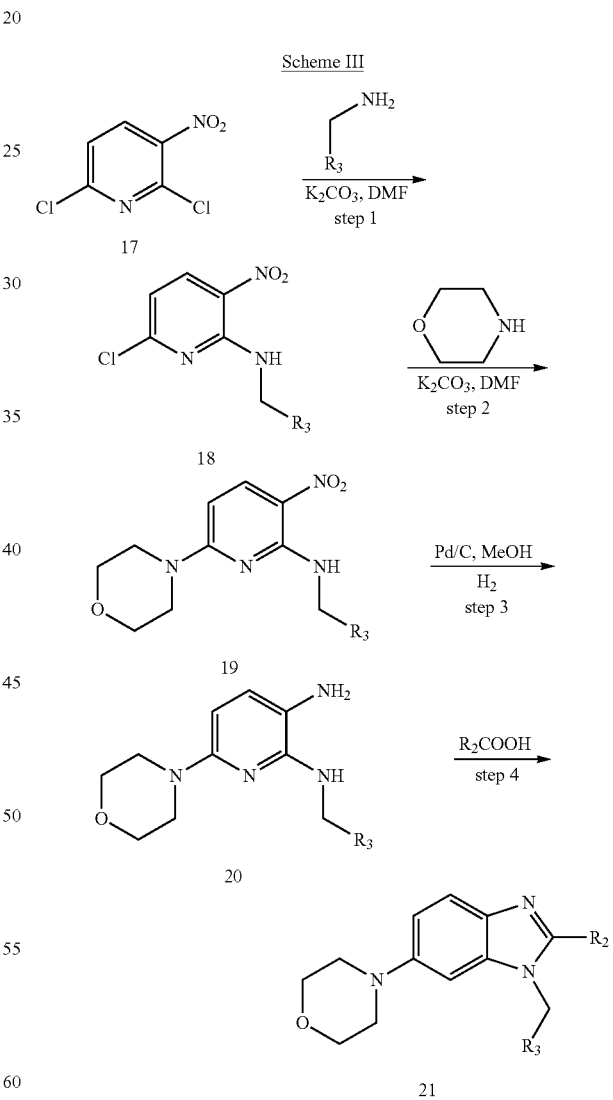

Oxidation of 2-chloro-4-methyl-5-nitropyridine (8) with chromium trioxide can provide 2-chloro-5-nitroisonicotinic acid (9) that can be reacted with morpholine in the presence of $K_2CO_3$ in DMF to provide 2-morpholino-5-nitroisonicotinic acid (10). Aromatic amination with methoxylamine in the presence of potassium t-butoxide and copper acetate can then provide 2-amino-6-morpholino-3-nitroisonicotinic acid (11) that is then converted to the corresponding methyl ester. Reduction of the nitro group to diamine 13 is followed by Reaction of 2,6-dichloro-3-nitropyridine 17 with an alkyl amine ($R3CH_2NH_2$) in the presence of $K_2CO_3$ in DMF can provide compound 18 which is then reacted with excess morpholine to provide morpholine analog 19. Nitro-reduction with hydrogen, catalyzed by palladium on carbon, in MeOH is then followed by condensation and ring-closure by heating with a carboxylic acid (R2CO₂H) to provide the desired final compounds 21.

Experimental Procedures

Example 1

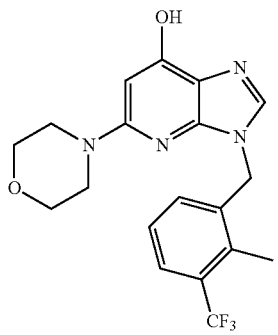 [SMILES: Cc1c(Cn2cnc3c(O)cc(N4CCOCC4)nc32)cccc1C(F)(F)F]

Preparation of 3-(2-methyl-3-(trifluoromethyl)benzyl)-5-morpholino-3H-imidazo[4,5-b]pyridin-7-ol a) 1H-imidazo[4,5-b]pyridine-4-N-oxide

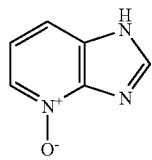

Hydrogen peroxide (3 mL, 29.4 mmol) was added to a suspension of 1H-imidazo[4,5-b]pyridine (2.6 g, 21.83 mmol) in Acetic Acid (12 mL). The mixture was stirred at 70° C. for 3 h, then at 50° C. overnight. The precipitate formed upon cooling was collected by filtration, washed with few mLs of cold water and dried to give 1H-imidazo[4,5-b]pyridine-4-N-oxide (2 g, 14.69 mmol, 67.3% yield). $^1$H NMR (400 MHz, METHANOL-d₄) δ ppm 8.46 (s, 1H), 8.34 (dd, J=6.44, 0.88 Hz, 1H), 7.88 (dd, J=8.21, 0.88 Hz, 1H), 7.39 (dd, J=8.21, 6.44 Hz, 1H) (2.01 (s, 3H); from AcOH).

b) 7-nitro-1H-imidazo[4,5-b]pyridine 4-oxide

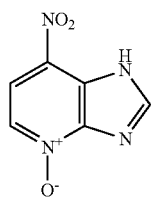

Nitric acid (20 mL, 448 mmol) was added to a solution of 1H-imidazo[4,5-b]pyridine-4-N-oxide (4.2 g, 30.9 mmol) in Trifluoroacetic acid (TFA) (29 mL) cooled at 0° C. The reaction mixture was then heated at 90° C. for 3.5 h. After cooling it was neutralized by the addition of NH₄OH while cooling in an ice bath. The yellow precipitate was collected by filtration, washed with cold water and dried overnight in a vacuum oven at 45° C. to give 6-nitro-1-deazapurine N-oxide (2.2 g, 12.15 mmol, 39.4% yield). This material was used in the next step without further purification. $^1$H NMR (400 MHz, DMSO-d₆) δ ppm 8.00 (s, 1H), 7.90 (d, J=7.07 Hz, 1H), 7.71 (d, 1H).

c) 5,7-dichloro-3H-imidazo[4,5-b]pyridine

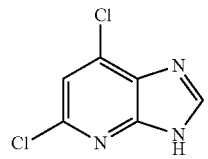 [SMILES: Clc1cc(Cl)c2nc[nH]c2n1]

7-nitro-1H-imidazo[4,5-b]pyridine 4-oxide (2.0 g, 11.04 mmol) was added portion-wise to a cooled (0° C.) solution of POCl₃ (30 mL, 322 mmol) in N,N-Dimethylformamide (DMF) (15 mL). The reaction mixture was then heated at 120° C. for 3 h. After cooling it was poured onto ice and then neutralized by the addition of 5 M NaOH. The mixture was extracted with EtOAc (3×75 mL). The combined extracts were washed with brine, dried over Na₂SO₄ and evaporated to give 5,7-dichloro-3H-imidazo[4,5-b]pyridine (1.86 g, 9.89 mmol, 90% yield) which was used in the next step without further purification. MS (ES⁺) m/e 188 (MH⁺). $^1$H NMR (400 MHz, METHANOL-d₄) δ ppm 8.45 (br. s., 1H), 7.46 (s, 1H).

d) 5,7-dichloro-3-(2-methyl-3-(trifluoromethyl)benzyl)-3H-imidazo[4,5-b]pyridine

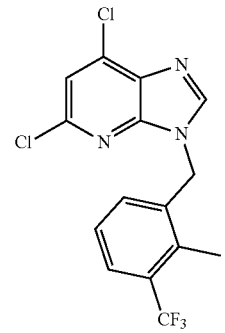 [SMILES: Cc1c(Cn2cnc3c(Cl)cc(Cl)nc32)cccc1C(F)(F)F]

Potassium carbonate (1139 mg, 8.24 mmol) was added to a solution of 5,7-dichloro-1H-imidazo[4,5-b]pyridine (500 mg, 2.66 mmol) in N,N-Dimethylformamide (DMF) (8.5 mL) and the mixture was stirred for 25 min. 1-(bromomethyl)-2-methyl-3-(trifluoromethyl)benzene (942 mg, 3.72 mmol) was then added and the reaction mixture was stirred at rt overnight. The mixture was partitioned between water and EtOAc. The aqueous layer was extracted with additional EtOAc (2×25 mL). The combined organic extracts were washed with brine, dried over Na₂SO₄ and evaporated. The residue was purified on silica gel (15 to 30% EtOAc in hexanes) to give 5,7-dichloro-3-{[2-methyl-3-(trifluoromethyl) phenyl]methyl}-3H-imidazo[4,5-b]pyridine (456 mg, 1.266 mmol, 47.6% yield) as an off-white powder. MS (ES⁺) m/e 359 (MH⁺) $^1$H NMR (400 MHz, DMSO-d₆) δ ppm 8.64 (s, 1H), 7.68 (s, 1H), 7.66 (d, J=8.08 Hz, 1H), 7.33 (t, J=7.71 Hz, 1H), 7.07 (d, J=7.83 Hz, 1H), 5.62 (s, 2H) (Ar—CH₃ hidden under DMSO peak).

e) 5-Chloro-7-(methyloxy)-3-{[2-methyl-3-(trifluoromethyl)phenyl]methyl}-3H-imidazo[4,5-b]pyridine

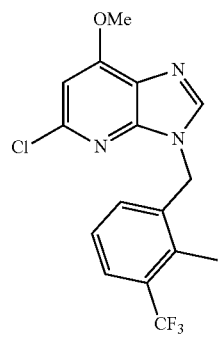 [SMILES: COc1cc(Cl)nc2c1ncn2Cc1cccc(C(F)(F)F)c1C]

5,7-dichloro-3-{[2-methyl-3-(trifluoromethyl)phenyl]methyl}-3H-imidazo[4,5-b]pyridine (200 mg, 0.555 mmol) was suspended in Methanol (1.5 mL), sodium methoxide (0.150 mL, 0.656 mmol) was added and the mixture was irradiated in a microwave oven for 90 min at 110° C. Conversion to desired product was observed by LC/MS (5,7-dimethoxy product, 5-methoxy isomer and 7-OH-5-Cl derivative observed by mass as well). The mixture was diluted with water and the precipitate formed was collected by filtration, washed with water and dried. The solid was purified on silica gel (ISCO 0-60% EtOAc in hexanes) to give 5-chloro-7-(methyloxy)-3-{[2-methyl-3-(trifluoromethyl)phenyl]methyl}-3H-imidazo[4,5-b]pyridine (125 mg, 0.351 mmol, 63.3% yield) as a white powder. Additional material was prepared from 120 mg of 5,7-dichloro-3-{[2-methyl-3-(trifluoromethyl)phenyl]methyl}-3H-imidazo[4,5-b]pyridine, irradiated in a microwave for 30 min at 110° C. in the presence of NaOMe. After work-up, 5-chloro-7-(methyloxy)-3-{[2-methyl-3-(trifluoromethyl)phenyl]methyl}-3H-imidazo[4,5-b]pyridine (109 mg, 0.306 mmol, 55.2% yield) was obtained and carried on without further purification to the next step. MS (ES⁺) m/e 356 (MH⁺).

f) 3-(2-methyl-3-(trifluoromethyl)benzyl)-5-morpholino-3H-imidazo[4,5-b]pyridin-7-ol 5-chloro-7-(methyloxy)-3-{[2-methyl-3-(trifluoromethyl)phenyl]methyl}-3H-imidazo[4,5-b]pyridine (45 mg, 0.126 mmol) was suspended in 1.5 mL of morpholine in a microwave vial and the mixture was irradiated in a microwave oven at 130° C. for 45 min, then for additional 3 h, another 3 h and then additional 12 h. Product is slowly forming (as observed by LC/MS) going through the formation of the 7-hydroxy derivative first. The mixture was then irradiated for 3 h at 200° C., to provide complete conversion to the desired product. An additional aliquot of 5-chloro-7-(methyloxy)-3-{[2-methyl-3-(trifluoromethyl)phenyl]methyl}-3H-imidazo[4,5-b]pyridine (60 mg, 0.169 mmol) was suspended in morpholine (1.5 mL) and irradiated in a microwave oven at 200° C. for 3 h. The reaction was not completed, so it was irradiated again in the microwave at 200° C. for 150 min. The two reaction mixtures were combined and diluted with water and 1 N HCl was added to pH 4-5. The precipitate formed was collected by filtration, washed with water and dried. The solid was dissolved in DMSO and purified by Reverse phase-HPLC (25 to 80% AcCN in water plus 0.1% TFA). Two peaks closely eluted on the HPLC and were isolated for the product. The slower retention time peak presented 2% impurity so it was kept separated. The collected fractions were neutralized by the addition of NaHCO₃ sat sol and the solvent volume was reduced to ½-⅓ of the original. The precipitates were collected washed with water and dried in a vacuum oven at 45° C. for 5 h to give 3-{[2-methyl-3-(trifluoromethyl)phenyl]methyl}-5-(4-morpholinyl)-3H-imidazo[4,5-b]pyridin-7-ol (21 mg, 0.052 mmol, 17.77% yield) which was submitted for testing, and the less pure sample of 3-{[2-methyl-3-(trifluoromethyl)phenyl]methyl}-5-(4-morpholinyl)-3H-imidazo[4,5-b]pyridin-7-ol (18 mg, 0.046 mmol, 15.54% yield), which was stored as is. MS (ES⁺) m/e 393 (MH⁺); ¹H NMR (400 MHz, DMSO-d₆) δ ppm 10.85 (br. s., 1H), 7.99 (s, 1H), 7.62 (d, J=8.08 Hz, 1H), 7.34 (t, J=7.83 Hz, 1H), 7.26 (d, J=7.58 Hz, 1H), 6.07 (s, 1H), 5.41 (s, 2H), 3.57-3.76 (m, 4H), 3.24-3.40 (m, 4H), (CH₃ peak under DMSO peak).

Example 2

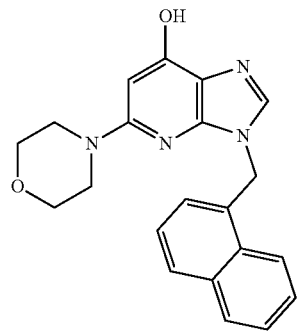 [SMILES: Oc1cc(N2CCOCC2)nc2c1ncn2Cc1cccc2ccccc12]

Preparation of 5-morpholino-3-(naphthalen-1-ylmethyl)-3H-imidazo[4,5-b]pyridin-7-ol a) 5,7-dichloro-3-(1-naphthalenylmethyl)-3H-imidazo[4,5-b]pyridine

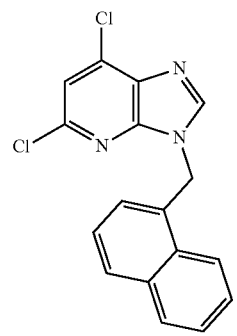 [SMILES: Clc1cc(Cl)c2ncn(Cc3cccc4ccccc34)c2n1]

Potassium carbonate (798 mg, 5.77 mmol) was added to a solution of 5,7-dichloro-1H-imidazo[4,5-b]pyridine (350 mg, 1.862 mmol) (5,7-dichloro-3H-imidazo[4,5-b]pyridine, obtained as described in example 1) in N,N-Dimethylformamide (DMF) (6.5 mL) and the mixture was stirred for 25 min.

1-(bromomethyl)naphthalene (576 mg, 2.61 mmol) was then added and the reaction mixture was stirred at rt overnight. The mixture was poured onto water and the precipitate formed was collected by filtration. The residue was purified on silica gel (15 to 30% EtOAc in hexanes) to give 5,7-dichloro-3-(1-naphthalenylmethyl)-3H-imidazo[4,5-b]pyridine (160 mg, 0.488 mmol, 26.2% yield) as a light yellow powder. MS (ES+) m/e 328 (MH+); 1H NMR (400 MHz, DMSO-d6) δ ppm 8.67 (s, 1H), 8.25 (d, J=8.08 Hz, 1H), 7.97-8.03 (m, 1H), 7.92 (d, J=8.34 Hz, 1H), 7.66-7.70 (m, 1H), 7.56-7.66 (m, 2H), 7.41-7.49 (m, 1H), 7.11 (d, J=6.32 Hz, 1H), 6.00 (s, 2H)

b) 5-Chloro-7-(methyloxy)-3-(1-naphthalenylmethyl)-3H-imidazo[4,5-b]pyridine

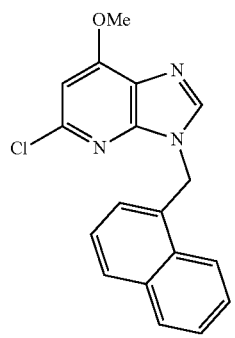 [SMILES: COc1cc(Cl)nc2c1ncn2Cc1cccc2ccccc12]

5,7-Dichloro-3-(1-naphthalenylmethyl)-3H-imidazo[4,5-b]pyridine (150 mg, 0.457 mmol) and sodium methoxide (0.157 mL, 0.686 mmol) in Methanol (1.5 mL) were irradiated in a microwave oven for 1 h at 110° C. The mixture was diluted with water, the precipitate was collected, washed with water, dried to give 5-chloro-7-(methyloxy)-3-(1-naphthalenylmethyl)-3H-imidazo[4,5-b]pyridine (143 mg, 0.318 mmol, 69.6% yield) which was used as is in the next step. MS (ES+) m/e 324 (MH+); 1H NMR (400 MHz, DMSO-d6) δ ppm 8.36 (s, 1H), 8.24 (d, J=7.83 Hz, 1H), 7.95-8.03 (m, 1H), 7.91 (d, J=8.08 Hz, 1H), 7.60 (qd, J=7.20, 5.43 Hz, 2H), 7.44 (dd, J=8.21, 7.20 Hz, 1H), 7.02 (d, J=7.07 Hz, 1H), 6.99 (s, 1H), 5.93 (s, 2H), 4.10 (s, 3H).

c) 5-morpholino-3-(naphthalen-1-ylmethyl)-3H-imidazo[4,5-b]pyridin-7-ol

A mixture of 5-chloro-7-(methyloxy)-3-(1-naphthalenylmethyl)-3H-imidazo[4,5-b]pyridine (140 mg, 0.432 mmol) and morpholine (2.5 mL, 28.7 mmol) was irradiated in a microwave oven for 4 h at 200° C. The mixture was diluted with water and the pH was adjusted to ca. 7 by the addition of 1 N HCl. The precipitate formed was collected, washed with water and air dried. It was then dissolved in DMSO and purified by RP-HPLC (Gilson, 25-80% AcCN in water plus 0.1% TFA). The fractions containing product were collected, neutralized by the addition of aqueous NaHCO3 sat sol and the volume was reduced to ½-⅓ of the original. The precipitate was collected by filtration, washed with water and dried overnight in a vacuum oven at 45° C. to give 5-(4-morpholinyl)-3-(1-naphthalenylmethyl)-3,4-dihydro-7H-imidazo[4,5-b]pyridin-7-one (45 mg, 0.122 mmol, 28.3% yield). MS (ES+) m/e 361 (MH+); 1H NMR (400 MHz, DMSO-d6) δ ppm 10.83 (br. s., 1H), 8.32-8.47 (m, 1H), 8.00 (s, 1H), 7.94-7.98 (m, 1H), 7.89 (d, J=8.08 Hz, 1H), 7.52-7.61 (m, 2H), 7.47 (dd, J=8.08, 7.07 Hz, 1H), 7.35 (d, J=6.32 Hz, 1H), 6.07 (s, 1H), 5.77 (s, 2H), 3.65-3.75 (m, 4H), 3.35-3.43 (m, 4H)

Example 3

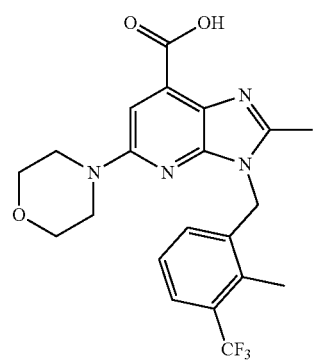 [SMILES: Cc1c(Cn2c(C)nc3c(C(=O)O)cc(N4CCOCC4)nc32)cccc1C(F)(F)F]

Preparation of 2-methyl-3-(2-methyl-3-(trifluoromethyl)benzyl)-5-morpholino-3H-imidazo[4,5-b]pyridine-7-carboxylic acid a) 2-chloro-5-nitroisonicotinic acid

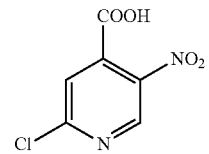 [SMILES: O=C(O)c1cc(Cl)ncc1[N+](=O)[O-]]

2-chloro-4-methyl-5-nitropyridine (31 g, 180 mmol) was dissolved in conc.H2SO4 (300 mL) and the resulting mixture was cooled to 0° C. CrO3 (59.4 g, 594 mmol) was added to the solution. After stirring for 1 h at 0° C., the mixture was warmed up to room temperature and stirred overnight. It was poured into ice-water (1 L). The mixture was warmed up to room temperature and filtered. The solid was then washed with water (2 L) and dried in vacuo to afford the desired product as a white solid (28.5 g, 78%); LC/MS: MS (ES+) m/e 203 (MH+); 1H NMR (300 MHz, DMSO-d6) δ ppm 8.04 (s, 1H), 9.16 (s, 1H).

b) 2-morpholino-5-nitroisonicotinic acid

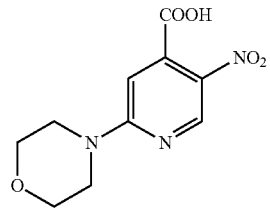 [SMILES: O=C(O)c1cc(N2CCOCC2)ncc1[N+](=O)[O-]]

A mixture of 2-chloro-5-nitroisonicotinic acid (28.5 g, 141 mmol), morpholine (36.8 g, 423 mmol) and k2CO3 (58.4 g, 423 mmol) was stirred at 100° C. for 4 h. The mixture was cooled to room temperature and poured into water (1.5 L). It was acidified with 4N HCl to pH=1 and extracted with EA (1 L×3). The combined organic layers were washed with brine (1 L×5), then dried over anhydrous Na$_2$SO$_4$, filtered and concentrated in vacuo to afford the desired product as a yellow solid (27 g, 76%); LC/MS: MS (ES$^+$) m/e 254 (MH$^+$); $^1$H NMR (300 MHz, DMSO-d$_6$) δ ppm 3.68 (t, J=4.8 Hz, 1H), 3.77 (t, J=4.8 Hz, 4H), 6.99 (s, 1H), 8.91 (s, 1H).

c) 2-amino-6-morpholino-3-nitroisonicotinic acid

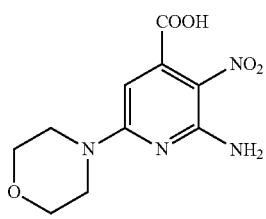 [SMILES: Nc1nc(N2CCOCC2)cc(C(=O)O)c1[N+](=O)[O-]]

To a solution of Cu(OAc)$_2$ (1.01 g, 5.6 mmol) and t-BuOK (21.95 g, 196 mmol) in DMF (200 mL) was added a solution of 2-morpholino-5-nitroisonicotinic acid (5.66 g, 28 mmol) and NH$_2$CH$_3$.HCl (4.65 g, 56 mmol) in DMF (100 mL) at 60° C. dropwise. The mixture was then stirred at 60° C. for 16 h. LCMS showed the desired product. It was cooled to room temperature and filtered. The filter cake was dissolved with water (250 mL) and acidified with aq. HCl solution to pH=1. It was then extracted with DCM/MeOH (400/100 mL×8). The organic layer was concentrated in vacuo. The residue was purified by silica gel chromatography eluted with MeOH/DCM=1/10 to afford the crude product as a black oil (4.5 g); LC/MS: MS (ES$^+$) m/e 269 (MH$^+$).

d) methyl 2-amino-6-morpholino-3-nitroisonicotinate

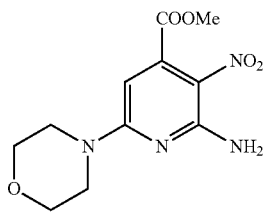

A mixture of 2-amino-6-morpholino-3-nitroisonicotinic acid (12.3 g, 45.9 mmol), HATU (19.2 g, 50.5 mmol), MeOH (14.7 g, 459 mmol) and Et$_3$N (13.9 g, 137.7 mmol) in THF (300 mL) was stirred at room temperature for 16 h. The solvent was removed in vacuo and the residue was diluted with EA (500 mL). It was then washed with brine (500 mL×3). The organic layer was then concentrated in vacuo. The residue was then purified by chromatography on silica gel eluted with MeOH/DCM=1/100 to afford the crude product as a yellow solid (4.8 g, 37%); LC/MS: MS (ES$^+$) m/e 283 (MH$^+$).

e) methyl 2,3-diamino-6-morpholinoisonicotinate

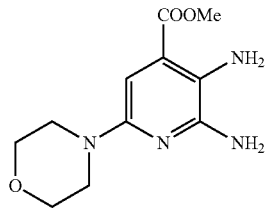 [SMILES: COC(=O)c1cc(N2CCOCC2)nc(N)c1[N+](=O)[O-]]

A mixture of methyl 2-amino-6-morpholino-3-nitroisonicotinate (4.8 g, 17 mmol) and 10% Pd/C (480 mg) in MeOH (100 mL) and CH$_3$COOH (50 mL) was stirred at room temperature for 16 h with connection to a balloon of H$_2$. LCMS showed no methyl 2-amino-6-morpholino-3-nitroisonicotinate left and the desired product formed. It was then filtered and the filtrate was concentrated in vacuo. The residue (4.3 g) was used for next step without purification. LC/MS: MS (ES$^+$) m/e 253 (MH$^+$).

f) methyl 2-methyl-5-morpholino-3H-imidazo[4,5-b]pyridine-7-carboxylate

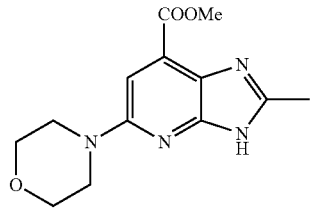 [SMILES: COC(=O)c1cc(N2CCOCC2)nc2[nH]c(C)nc12]

A solution of methyl 2,3-diamino-6-morpholinoisonicotinate (4.3 g, 17 mmol) in CH$_3$COOH (100 mL) was refluxed for 16 h. LCMS showed no methyl 2,3-diamino-6-morpholinoisonicotinate left and the desired product formed. It was cooled to room temperature and the solvent was removed in vacuo. The residue was then purified by chromatography on silica gel eluted with MeOH/DCM=1/50 to afford the desired product as a black solid (1.07 g, 23%); LC/MS: MS (ES$^+$) m/e 277 (MH$^+$); $^1$H NMR (300 MHz, CDCl$_3$) δ ppm 2.69 (s, 3H), 3.58 (t, J=4.8 Hz, 4H), 3.86 (t, J=4.8 Hz, 4H), 4.02 (s, 3H), 7.12 (s, 1H).

g) methyl 2-methyl-3-(2-methyl-3-(trifluoromethyl)benzyl)-5-morpholino-3H-imidazo[4,5-b]pyridine-7-carboxylate

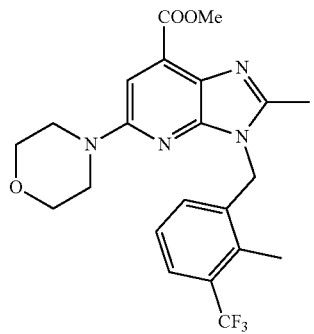 [SMILES: COC(=O)c1cc(N2CCOCC2)nc2c1nc(C)n2Cc1cccc(C(F)(F)F)c1C]

A mixture of methyl 2-methyl-5-morpholino-3H-imidazo[4,5-b]pyridine-7-carboxylate (207 mg, 0.75 mmol), 1-(bromomethyl)-2-methyl-3-(trifluoromethyl)benzene (285 mg, 1.125 mmol) and Na$_2$CO$_3$ (239 mg, 2.25 mmol) in DMF (10 mL) was stirred at 80° C. for 3 h. TLC showed no methyl 2-methyl-5-morpholino-3H-imidazo[4,5-b]pyridine-7-carboxylate left. It was cooled to room temperature and poured into water (50 mL) and filtered. The solid was dissolved with DCM (150 mL) and it was washed with brine (100 mL×3) and the organic layer was dried over anhydrous Na$_2$SO$_4$, filtered and concentrated in vacuo to afford the desired product as a brown solid (320 mg, 95%); LC/MS: MS (ES⁺) m/e 449 (MH⁺); ¹H NMR (300 MHz, DMSO-$d_6$) δ ppm 2.40 (s, 3H), 2.51 (s, 3H), 3.41 (t, J=4.8 Hz, 4H), 3.68 (t, J=4.8 Hz, 4H), 3.92 (s, 3H), 5.50 (s, 2H), 6.90 (d, J=7.8 Hz, 1H), 7.07 (s, 1H), 7.28 (t, J=7.5 Hz, 1H), 7.62 (d, J=7.8 Hz, 1H).

h) 2-methyl-3-(2-methyl-3-(trifluoromethyl)benzyl)-5-morpholino-3H-imidazo[4,5-b]pyridine-7-carboxylic acid A mixture of methyl 2-methyl-3-(2-methyl-3-(trifluoromethyl)benzyl)-5-morpholino-3H-imidazo[4,5-b]pyridine-7-carboxylate (310 mg, 0.69 mmol) in 2N LiOH (15 mL) and THF (15 mL) was stirred at 50° C. for 8 h. It was cooled to room temperature and the precipitate was collected by filtration. It was then poured into water (50 mL) and the suspension was acidified with formic acid to pH=1. It was filtered and the solid was purified by chromatography on silica gel eluted with MeOH/DCM=1/5 to afford the desired product as a gray solid (184 mg, 61%); LC/MS: MS (ES⁺) m/e 435 (MH⁺); ¹H NMR (300 MHz, DMSO-$d_6$) δ ppm 2.54 (s, 3H), 2.79 (s, 3H), 3.51 (s, 4H), 3.67 (s, 4H), 5.67 (s, 2H), 7.20 (d, J=10.2 Hz, 1H), 7.35 (t, J=7.8 Hz, 1H), 7.42 (s, 1H), 7.69 (d, J=10.2 Hz, 1H).

Example 4

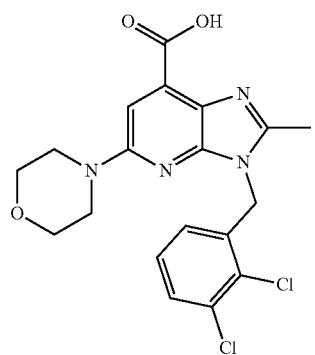

Preparation of 3-(2,3-dichlorobenzyl)-2-methyl-5-morpholino-3H-imidazo[4,5-b]pyridine-7-carboxylic acid a) methyl 3-(2,3-dichlorobenzyl)-2-methyl-5-morpholino-3H-imidazo[4,5-b]pyridine-7-carboxylate

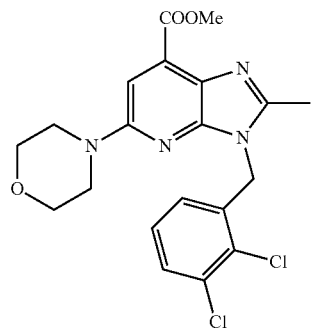 [SMILES: COC(=O)c1cc(N2CCOCC2)nc2c1nc(C)n2Cc1cccc(Cl)c1Cl]

A mixture of methyl 2-methyl-5-morpholino-3H-imidazo[4,5-b]pyridine-7-carboxylate (200 mg, 0.72 mmol), 1-(bromomethyl)-2,3-dichlorobenzene), prepared as described in Example 3, step f, (259 mg, 1.08 mmol and Na₂CO₃ (229 mg, 2.16 mmol) in DMF (10 mL) was stirred at 80° C. for 16 h. The reaction mixture was cooled to room temperature and poured into water (100 mL). It was extracted with EtOAc (100 mL×2). The combined organic layers were washed with brine (100 mL×3), dried over anhydrous Na₂SO₄, filtered and concentrated in vacuo. The residue was purified by chromatography on silica gel eluted with MeOH/DCM=1/60 to afford the desired product as a black solid (243 mg, 78%); LC/MS: MS (ES⁺) m/e 435 (MH⁺); ¹H NMR (300 MHz, DMSO-$d_6$) δ ppm 2.46 (s, 3H), 3.40 (t, J=4.2 Hz, 4H), 3.67 (t, J=4.2 Hz, 4H), 3.92 (s, 3H), 5.50 (s, 2H), 6.60 (d, J=7.8 Hz, 1H), 7.06 (s, 1H), 7.27 (t, J=7.8 Hz, 1H), 7.60 (d, J=7.8 Hz, 1H).

b) 3-(2,3-dichlorobenzyl)-2-methyl-5-morpholino-3H-imidazo[4,5-b]pyridine-7-carboxylic acid A mixture of methyl 3-(2,3-dichlorobenzyl)-2-methyl-5-morpholino-3H-imidazo[4,5-b]pyridine-7-carboxylate (239 mg, 0.55 mmol) in 2N LiOH (15 mL) and THF (15 mL) was stirred at 60° C. for 5 h. It was cooled to room temperature and the precipitate was collected by filtration. It was then poured into water (50 mL) and the suspension was acidified with formic acid to pH=1. It was filtered and the solid was washed with water to afford the desired product as a gray solid (146 mg, 63%); LC/MS: MS (ES⁺) m/e 421 (MH⁺); ¹H NMR (300 MHz, DMSO-$d_6$) δ ppm 2.46 (s, 3H), 3.39 (t, J=4.8 Hz, 4H), 3.67 (t, J=4.8 Hz, 4H), 5.50 (s, 2H), 6.67 (d, J=4.5 Hz, 1H), 7.04 (s, 1H), 7.28 (t, J=7.5 Hz, 1H), 7.60 (d, J=4.5 Hz, 1H), 8.14 (s, 1H).

Example 5

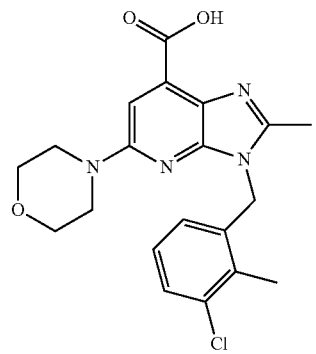 [SMILES: Cc1c(Cl)cccc1Cn1c(C)nc2c(C(=O)O)cc(N3CCOCC3)nc21]

Preparation of 3-(3-chloro-2-methylbenzyl)-2-methyl-5-morpholino-3H-imidazo[4,5-b]pyridine-7-carboxylic acid a) methyl 3-(3-chloro-2-methylbenzyl)-2-methyl-5-morpholino-3H-imidazo[4,5-b]pyridine-7-carboxylate

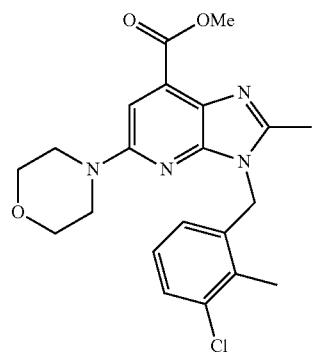 [SMILES: COC(=O)c1cc(N2CCOCC2)nc2c1nc(C)n2Cc1cccc(Cl)c1C]

A mixture of methyl 2-methyl-5-morpholino-3H-imidazo[4,5-b]pyridine-7-carboxylate (200 mg, 0.72 mmol), prepared as described in Example 3, step f, 1-(bromomethyl)-3-chloro-2-methylbenzene (237 mg, 1.08 mmol) and Na₂CO₃ (153 mg, 1.44 mmol) in DMF (10 mL) was stirred at 80° C. for 5 h. It was cooled to room temperature and poured into water (100 mL). It was extracted with EA (100 mL×2). The combined organic layers were washed with brine (100 mL×3), dried over anhydrous Na₂SO₄, filtered and concentrated in vacuo. The residue was purified by chromatography on silica gel eluted with MeOH/DCM=1/60 to afford the desired product as a black solid (239 mg, 80%); LC/MS: MS (ES⁺) m/e 415 (MH⁺); ¹H NMR (300 MHz, DMSO-d₆) δ ppm 2.39 (s, 3H), 2.44 (s, 3H), 3.42 (t, J=4.8 Hz, 4H), 3.69 (t, J=4.8 Hz, 4H), 3.92 (s, 3H), 5.45 (s, 2H), 6.37 (d, J=7.8 Hz, 1H), 7.07-7.12 (m, 2H), 7.36 (d, 1H).

b) 3-(3-chloro-2-methylbenzyl)-2-methyl-5-morpholino-3H-imidazo[4,5-b]pyridine-7-carboxylic acid A mixture of methyl 3-(3-chloro-2-methylbenzyl)-2-methyl-5-morpholino-3H-imidazo[4,5-b]pyridine-7-carboxylate (239 mg, 0.58 mmol) in 2N LiOH (15 mL) and THF (15 mL) was stirred at 60° C. for 5 h. It was cooled to room temperature and the precipitate was collected by filtration. It was then poured into water (100 mL) and the suspension was acidified with formic acid to pH=1. It was filtered and the solid was washed with water to afford the desired product as a gray solid (163 mg, 71%). LC/MS: MS (ES⁺) m/e 401 (MH⁺); ¹H NMR (300 MHz, DMSO-d₆) δ ppm 2.36 (s, 3H), 2.44 (s, 3H), 3.41 (s, 4H), 3.69 (s, 4H), 5.44 (s, 2H), 6.40 (d, J=7.5 Hz, 1H), 7.05-7.11 (m, 2H), 7.35 (d, 1H).

Example 6

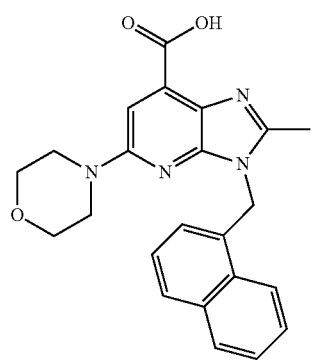 [SMILES: Cc1nc2c(C(=O)O)cc(N3CCOCC3)nc2n1Cc1cccc2ccccc12]

Preparation of 2-methyl-5-morpholino-3-(naphthalen-1-ylmethyl)-3H-imidazo[4,5-b]pyridine-7-carboxylic acid a) methyl 2-methyl-5-morpholino-3-(naphthalen-1-ylmethyl)-3H-imidazo[4,5-b]pyridine-7-carboxylate

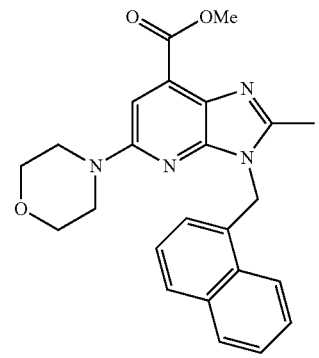 [SMILES: COC(=O)c1cc(N2CCOCC2)nc2c1nc(C)n2Cc1cccc2ccccc12]

A mixture of methyl 2-methyl-5-morpholino-3H-imidazo[4,5-b]pyridine-7-carboxylate (138 mg, 0.5 mmol), 1-(bromomethyl)naphthalene (166 mg, 0.75 mmol) and Na₂CO₃ (138 mg, 1 mmol) in DMF (10 mL) was stirred at 80° C. for 5 h. It was cooled to room temperature and poured into water (50 mL). It was extracted with EA (100 mL×2). The combined organic layers were washed with brine (100 mL×2), dried over anhydrous Na₂SO₄, filtered and concentrated in vacuo. The residue was purified by chromatography on silica gel eluted with 100% EA to afford the desired product as a black solid (143 mg, 69%); LC/MS: MS (ES⁺) m/e 417 (MH⁺); ¹H NMR (300 MHz, DMSO-d₆) δ ppm 2.42 (s, 3H), 3.42 (t, J=4.5 Hz, 4H), 3.67 (t, J=4.5 Hz, 4H), 3.93 (s, 3H), 5.92 (s, 2H), 6.70 (d, J=7.2 Hz, 1H), 7.09 (s, 1H), 7.39 (t, J=7.5 Hz, 1H), 7.57-7.65 (m, 2H), 7.87 (d, J=9.0 Hz, 1H), 7.90 (d, J=9.0 Hz, 1H), 8.34 (d, J=7.2 Hz, 1H).

b) 2-methyl-5-morpholino-3-(naphthalen-1-ylmethyl)-3H-imidazo[4,5-b]pyridine-7-carboxylic acid A mixture of methyl 2-methyl-5-morpholino-3-(naphthalen-1-ylmethyl)-3H-imidazo[4,5-b]pyridine-7-carboxylate (134 mg, 0.32 mmol) in 2N LiOH (15 mL) and THF (15 mL) was stirred at 50° C. for 5 h. It was cooled to room temperature and the precipitate was collected by filtration. It was then poured into water (100 mL) and the suspension was acidified with formic acid to pH=1. It was filtered and the solid was purified by chromatography on silica gel eluted with MeOH/DCM=1/5 to afford the crude product. It was then made a further purification by prep-HPLC to afford the desired product as a yellow solid (64 mg, 50%); LC/MS: MS (ES⁺) m/e 403 (MH⁺); ¹H NMR (300 MHz, DMSO-d₆) δ ppm 2.63 (s, 3H), 3.48 (t, J=4.2 Hz, 4H), 3.65 (t, J=4.2 Hz, 4H), 6.03 (s, 2H), 6.97 (d, J=7.8 Hz, 1H), 7.28 (s, 1H), 7.42 (t, J=7.5 Hz, 1H), 7.58-7.67 (m, 2H), 7.91 (d, J=7.8 Hz, 1H), 8.01 (d, J=7.8 Hz, 1H), 8.33 (d, J=7.8 Hz, 1H).

Example 7

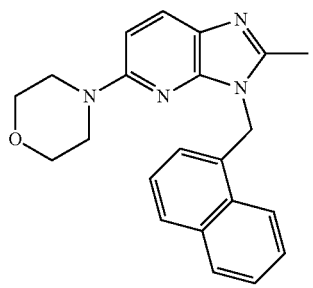 [SMILES: Cc1nc2ccc(N3CCOCC3)nc2n1Cc1cccc2ccccc12]

Preparation of 4-(2-methyl-3-(naphthalen-1-ylmethyl)-3H-imidazo[4,5-b]pyridin-5-yl)morpholine a) 6-chloro-N-(naphthalen-1-ylmethyl)-3-nitropyridin-2-amine

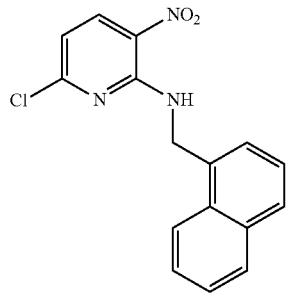 [SMILES: O=[N+]([O-])c1ccc(Cl)nc1NCc1cccc2ccccc12]

A mixture of 2,6-dichloro-3-nitropyridine (3.86 g, 20 mmol), naphthalen-1-ylmethanamine (3.14 g, 20 mmol) and K$_2$CO$_3$ (4.14 g, 30 mmol) in DMF (100 mL) was stirred at 80° C. for 3 h. It was cooled to room temperature and poured into water (500 mL). It was extracted with EtOAc (300 mL×2). The combined organic layers were washed with brine (300 mL×3), dried over anhydrous Na$_2$SO$_4$, filtered and concentrated in vacuo. The residue was purified by chromatography on silica gel eluted with EtOAc/Pet ether=1/6 to afford the desired product as a yellow solid (3.21 g, 51%); LC/MS: MS (ES$^+$) m/e 314 (MH$^+$); $^1$H NMR (300 MHz, DMSO-d$_6$) δ ppm 5.21 (d, J=6.0 Hz, 2H), 6.80 (d, J=8.7 Hz, 1H), 7.43-7.63 (m, 4H), 7.85 (d, J=8.1 Hz, 1H), 7.97 (d, J=8.1 Hz, 1H), 8.26 (d, J=8.1 Hz, 1H), 8.46 (d, J=8.7 Hz, 1H), 9.20 (t, J=5.7 Hz, 1H).

b) 6-morpholino-N-(naphthalen-1-ylmethyl)-3-nitropyridin-2-amine

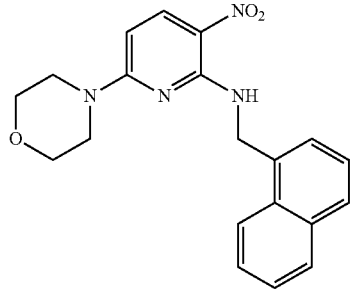 [SMILES: O=[N+]([O-])c1ccc(N2CCOCC2)nc1NCc1cccc2ccccc12]

A mixture of 6-chloro-N-(naphthalen-1-ylmethyl)-3-nitropyridin-2-amine (3.21 g, 10.2 mmol), morpholine (2.66 g, 30.6 mmol) and K$_2$CO$_3$ (2.11 g, 15.3 mmol) in DMF (50 mL) was stirred at 80° C. for 1 h. It was cooled to room temperature and poured into water (300 mL). It was extracted with EA (300 mL×2). The combined organic layers were washed with brine (300 mL×3), dried over anhydrous Na$_2$SO$_4$, filtered and concentrated in vacuo. The residue was purified by chromatography on silica gel eluted with EtOAc/Pet ether=1/1 to afford the desired product as a yellow solid (3.56 g, 96%); LC/MS: MS (ES$^+$) m/e 365 (MH$^+$); $^1$H NMR (300 MHz, DMSO-d$_6$) δ ppm 3.53 (t, J=4.2 Hz, 4H), 3.60 (t, J=4.2 Hz, 4H), 5.19 (d, J=5.7 Hz, 2H), 6.33 (d, J=9.6 Hz, 1H), 7.44-7.61 (m, 4H), 7.85 (d, J=7.5 Hz, 1H), 7.97 (d, J=7.5 Hz, 1H), 8.12 (d, J=9.6 Hz, 1H), 8.21 (d, J=7.5 Hz, 1H), 9.25 (t, J=5.7 Hz, 1H).

c) 6-morpholino-N2-(naphthalen-1-ylmethyl)pyridine-2,3-diamine

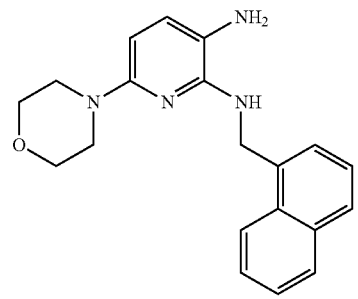

A mixture of 6-morpholino-N-(naphthalen-1-ylmethyl)-3-nitropyridin-2-amine (3.56 g, 9.78 mmol) and 10% Pd/C (300 mg) in MeOH (200 mL) was stirred at room temperature for 3 h under a balloon pressure of H$_2$. It was filtered and the filtrate was concentrated in vacuo to afford the desired as a dark-green solid (3.2 g, 98%); LC/MS: MS (ES$^+$) m/e 335 (MH$^+$); $^1$H NMR (300 MHz, DMSO-d$_6$) δ ppm 3.10 (t, J=4.5 Hz, 4H), 3.60 (t, J=4.5 Hz, 4H), 4.11 (s, 2H), 4.98 (d, J=5.4 Hz, 2H), 5.79 (d, J=8.1 Hz, 1H), 5.97 (t, J=5.4 Hz, 1H), 6.71 (d, J=8.1 Hz, 1H), 7.42-7.53 (m, 4H), 7.81 (d, J=7.5 Hz, 1H), 7.93 (t, J=4.8 Hz, 1H), 8.21 (d, J=4.8 Hz, 1H).

d) 4-(2-methyl-3-(naphthalen-1-ylmethyl)-3H-imidazo[4,5-b]pyridin-5-yl)morpholine A mixture of 6-morpholino-N2-(naphthalen-1-ylmethyl)pyridine-2,3-diamine (3.2 g, 9.58 mmol) in CH$_3$COOH (50 mL) was refluxed for 16 h. The mixture was cooled to room temperature and concentrated in vacuo. The residue was purified by chromatography eluted with EtOAc/Pet Ether=1/1 and then recrystallized in EtOAc to afford the desired product as a pale solid (481 mg, 14%); LC/MS: MS (ES$^+$) m/e 359 (MH$^+$); $^1$H NMR (300 MHz, DMSO-d$_6$) δ ppm 2.36 (s, 3H), 3.39 (t, J=4.8 Hz, 4H), 3.67 (t, J=4.8 Hz, 4H), 5.87 (s, 2H), 6.72-6.77 (m, 2H), 7.37-7.42 (m, 1H), 7.56-7.65 (m, 2H), 7.80 (d, J=8.7 Hz, 1H), 7.87 (d, J=8.4 Hz, 1H), 7.98-8.01 (m, 1H), 8.36-8.39 (m, 1H).

Example 8

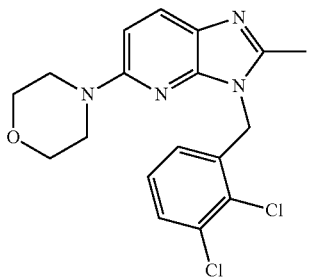 [SMILES: Cc1nc2ccc(N3CCOCC3)nc2n1Cc1cccc(Cl)c1Cl]

Preparation of 4-(3-(2,3-dichlorobenzyl)-2-methyl-3H-imidazo[4,5-b]pyridin-5-yl)morpholine a) 6-chloro-N-(2,3-dichlorobenzyl)-3-nitropyridin-2-amine

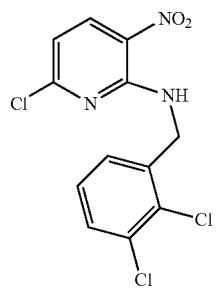 [SMILES: O=[N+]([O-])c1ccc(Cl)nc1NCc1cccc(Cl)c1Cl]

A mixture of 2,6-dichloro-3-nitropyridine (3.86 g, 20 mmol), (2,3-dichlorocyclohexa-1,3-dienyl)methanamine (3.52 g, 20 mmol) and $K_2CO_3$ (4.14 g, 30 mmol) in DMF (100 mL) was stirred at 80° C. for 3 h. It was cooled to room temperature and poured into water (500 mL). It was extracted with EtOAc (300 mL×2). The combined organic layers were washed with brine (300 mL×3), dried over anhydrous $Na_2SO_4$, filtered and concentrated in vacuo. The residue was purified by chromatography on silica gel eluted with EtOAc/Pet Ether=1/6 to afford the desired product as a yellow solid (3.37 g, 51%); LC/MS: MS (ES$^+$) m/e 332 (MH$^+$); $^1$H NMR (300 MHz, DMSO-d$_6$) δ ppm 4.82 (d, J=5.7 Hz, 2H), 6.84 (dd, J=0.9, 6.6 Hz, 1H), 7.28-7.34 (m, 2H), 7.55 (dd, J=2.1, 6.6 Hz, 1H), 8.48 (dd, J=0.9, 6.6 Hz, 1H), 9.22 (t, J=5.7 Hz, 1H).

b) N-(2,3-dichlorobenzyl)-6-morpholino-3-nitropyridin-2-amine

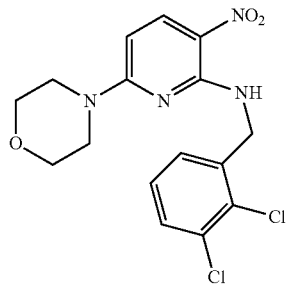 [SMILES: O=[N+]([O-])c1ccc(N2CCOCC2)nc1NCc1cccc(Cl)c1Cl]

A mixture of 6-chloro-N-(2,3-dichlorobenzyl)-3-nitropyridin-2-amine (3.37 g, 10.1 mmol), morpholine (2.64 g, 30.3 mmol) and $K_2CO_3$ (2.09 g, 15.15 mmol) in DMF (50 mL) was stirred at 80° C. for 1 h. The reaction was cooled to room temperature and poured into water (300 mL). It was extracted with EtOAc (300 mL×2). The combined organic layers were washed with brine (300 mL×3), dried over anhydrous $Na_2SO_4$, filtered and concentrated in vacuo. The residue was purified by chromatography on silica gel eluted with EtOAc/Pet Ether=1/1 to afford the desired product as a yellow solid (3.7 g, 96%); LC/MS: MS (ES$^+$) m/e 383 (MH$^+$); $^1$H NMR (300 MHz, DMSO-d$_6$) δ ppm 3.54 (s, 4H), 3.56 (s, 4H), 4.81 (d, J=5.7 Hz, 2H), 6.33 (d, J=9.6 Hz, 1H), 7.27-7.34 (m, 2H), 7.53 (dd, J=2.1, 6.9 Hz, 1H), 8.12 (d, J=9.6 Hz, 1H), 9.33 (t, J=6.3 Hz, 1H).

c) 4-(3-(2,3-dichlorobenzyl)-2-methyl-3H-imidazo[4,5-b]pyridin-5-yl)morpholine

To a refluxed solution of N-(2,3-dichlorobenzyl)-6-morpholino-3-nitropyridin-2-amine (1.15 g, 3 mmol) in $CH_3COOH$ (100 mL) was added iron powder (504 mg, 9 mmol) in portions. The mixture was then refluxed for 16 h and cooled to room temperature. It was filtered and the filtrate was concentrated in vacuo. The residue was then purified by chromatography on silica gel eluting with EtOAc/Pet ether=1/1 to afford the desired product as a pale solid (352 mg, 30%). LC/MS: MS (ES$^+$) m/e 377 (MH$^+$); $^1$H NMR (300 MHz, DMSO-d$_6$) δ ppm 2.41 (s, 3H), 3.36 (t, J=4.8 Hz, 4H), 3.67 (t, J=4.8 Hz, 4H), 5.46 (s, 2H), 6.63 (d, J=8.1 Hz, 1H), 6.72 (d, J=8.7 Hz, 1H), 7.28 (t, J=8.1 Hz, 1H), 7.59 (d, J=8.1 Hz, 1H), 7.78 (d, J=8.7 Hz, 1H).

Biological Assays

Compounds of the present invention were tested according to the following assays and found as inhibitors of PI3 kinases, particularly PI3Kβ. The activities (IC$_{50}$) of exemplified compounds range from about 1 nM to about 10 μM against PI3Kβ. The majority of the compounds were under 500 nM; the most active compounds were under 10 nM. The IC$_{50}$ value can be converted and presented as pIC$_{50}$ value.

HTRF In Vitro Profiling Assays for PI3K Inhibition

The PI3-Kinase profiling assays were developed to measure the compound-dependent inhibition of the alpha, beta, delta, and gamma isoforms of PI3Kin an in vitro catalytic assay. This assay was developed and optimized from a kit produced by Upstate (Millipore catalog #33-017). Briefly, this procedure utilizes a pre-formed HTRF (Homogeneous Time-Resolved Fluorescence energy transfer) complex between four binding partners: 1) biotinylated PIP3, 2) GST tagged pleckstrin homology (PH) domain, 3) Europium labeled anti-GST monoclonal antibody, and 4) Streptavidin-Allophycocyanin (APC). The native PIP3 produced by PI 3-Kinase activity displaces biotin-PIP3 from the PH domain, resulting in the dissociation of the HTRF complex and a decrease in the fluorescence signal. The format of this assay is the same for all 4 isoforms of PI3K; the differences lie in the concentration of enzyme used to achieve the most robust signal. The alpha and delta assays are run at 400 pM enzyme; the beta assay is at 200 pM enzyme and the gamma assay is run at 1 nM enzyme. In addition, the alpha, beta and delta assays are run with 150 mM NaCl while the gamma assay is run in the absence of NaCl. The ATP concentration is 100 uM in the alpha, beta, and delta assays and 15 uM ATP in the gamma assay. All reactions are run at 10 uM PIP2

Compounds were serially diluted (3-fold in 100% DMSO) across a 384-well polypropylene mother plate from column 1 to column 12 and column 13 to column 24, to yield 11 concentrations for each test compound. Columns 6 and 18 contain only DMSO. Once titrations were made, 0.054 was transferred to a 384-well low-volume assay plate (Greiner 784076). This assay plate contained three pharmacological controls (known PI3K inhibitors) and 3 assay controls: (1) Enzyme without inhibitor; (2) Buffer minus enzyme, and (3) Buffer minus enzyme plus native PIP3. DMSO was stamped into all wells of columns 6 and 18. PIP3 was added at 40 μM in 1× Reaction buffer (1 μL of 200 μM PIP3) to alternating rows of column 18 (wells 18 B, D, F, H, J, L, N, P). The no-enzyme control reactions were run in wells 18 A, C, E, G, I, K, M, O (0.14 of 100% DMSO).

The PI3-Kinase profiling assay was optimized using the HTRF kit provided by Upstate (Millipore). The assay kit contained seven reagents: 1) 4× Reaction Buffer; 2) native PIP2 (substrate); 3) Stop A (EDTA); 4) Stop B (Biotin-PIP3); 5) Detection Mix A (Streptavidin-APC); 6) Detection Mix B (Eu-labeled Anti-GST plus GST-tagged PH-domain); 7) Detection Mix C (KF). In addition, the following items were obtained or purchased: PI3Kinase (prepared by GSK BR&AD), dithiothreitol (Sigma, D-5545), Adenosine-5'-triphosphate (ATP, Teknova cat. #A0220), native PIP3 (1,2-dioctanoyl-sn-glycero-3-[phosphoinositil-3,4,5-triphosphate]tetraammonium salt (Avanti polar lipids, 850186P), DMSO (Sigma, 472301).

PI3Kinase Reaction Buffer was prepared by diluting the stock 1:4 with de-ionized water. Freshly prepared DTT was added at a final concentration of 5 mM on the day of use. Enzyme addition and compound pre-incubation were initiated by the addition of 2.5 μL of PI3K (at twice its final concentration) in 1× reaction buffer to all wells using a Multidrop Combi. Plates were incubated at room temperature for 15 minutes. Reactions were initiated by addition of 2.5 μL of 2× substrate solution (PIP2 and ATP in 1× reaction buffer) using a Multidrop Combi. Plates were incubated at room temperature for one hour. Reactions were quenched by the addition of 2.5 μL of stop solution (Stop A and Stop B pre-mixed at a ratio of 5:1, respectively) to all wells using the Multidrop Combi. The quenched reactions were then processed to detect product formation by adding 2.5 μL of Detection Solution to all wells using the Mulitdrop Combi (Detection mix C, Detection mix A, and Detection mix B combined together in an 18:1:1 ratio, i.e.: for a 6000 μL total volume, mix 5400 μL Detection mix C, 300 μL Detection mix A, and 300 μL Detection mix B. Note: this solution should be prepared 2 hours prior to use). Following a one hour incubation in the dark, the HTRF signal was measured on the Envision plate reader set for 330 nm excitation and dual emission detection at 620 nm (Eu) and 665 nm (APC).

The loss of the HTRF signal is due to the displacement of biotinylated-PIP3 from the PH domain by the PI3K-dependent conversion of PIP2 to PIP3. This loss of signal is non-linear with respect to both increasing product and time. This non-linear detection will impact accuracy of $IC_{50}$ calculations; therefore, there is a need for a correction factor to obtain more accurate $IC_{50}$ values. This correction is derived from the assay standards in the wells of column 6 and 18 of the assay plate.

All data were calculated using the ratio of acceptor (APC) to donor (Europium) fluorescence in each well of the assay plate. The percent inhibition for each compound concentration was calculated as follows: % inhibition=100*(fluorescence ratio−CtrlB)/(CtrlA−CtrlB) where CtrlA=(−) PI3Kinase reaction and CrtlB=PI3Kinase+DMSO.

An $IC_{50}$ was then calculated fitting the % inhibition data to the equation: % inhibition=min+(max−min)/(1+([inhibitor]/$IC_{50}$)^n) where min is the % inhibition with no inhibitor (typically 0%), max is the signal in the (−) Enzyme control, and n is the Hill slope (typically 1). Finally, the $IC_{50}$ was converted to $pIC_{50}$ ($pIC_{50}$=−log($IC_{50}$)), and the $pIC_{50}$ value was corrected by using plate controls and the equation below: $pIC_{50}$ (corrected)=$pIC_{50}$ (observed)+log 10((CtrlA−CtrlB)/(CtrlB−CtrlC)), where CtrlA and CtrlB are as defined above and CrtlC=10 μM PI(3,4,5)P3, 100% displacement of biotinylated PI(3,4,5)P3.

The compounds listed in Table 1 were tested generally according to the assays described herein. Table 1 lists the pIC50 values for either an experimental run or an average of two or more experimental runs with the examples shown.

TABLE 1

| Example # | MW | PI3K b $pIC_{50}$ |
|---|---|---|
| 1 | 392.38 | 8.8 |
| 2 | 360.42 | 8.5 |
| 3 | 434.42 | 8.3 |
| 4 | 421.28 | 8.3 |
| 5 | 400.86 | 8.8 |
| 6 | 402.45 | 8.8 |
| 7 | 358.44 | 8.2 |
| 8 | 377.27 | 7.4 |

Cellular Assays—Inhibition of Phosphorylation of AKT in PTEN Deficient Tumor Cell Line MDA-MB-468

Compounds were evaluated for their ability to inhibit downstream phosphorylation of AKT in MDA-MB-468 tumor cells. Breast cancer cells were plated, incubated for approximately 16-20 hours and then treated with compound for 30 minutes. Final DMSO concentration on all cells was 0.15%. The cells were washed with Tris buffer and lysed in MesoScale Discovery (MSD) lysis buffer containing protease and phosphatase inhibitors (included in MSD kit). MSD Ser473-AKT duplex plates (Cat #MS6000) were used according to the manufacturer's instructions and plates were read on a SECTOR™ Imager 6000 using MSD Workbench software. For analysis of the Ser473-pAKT concentration response curves, the data was normalized using the corresponding total AKT value (sum of pAKT and AKT signal) and plotted as the percent of the DMSO-treated control values. The data was fit in Graphpad Prism version 4 for Windows (Graphpad Software, San Diego, Calif.).

The compounds listed in Table 2 were tested generally according to the assays described herein. Table 2 lists the $IC_{50}$ values for either an experimental run or an average of two or more experimental runs with the examples shown.

TABLE 2

| Example # | MW | $IC_{50}$ pAKT (nM) MDA-MB-468 |
|---|---|---|
| 1 | 392.38 | 476.82 |
| 2 | 360.42 | 578.42 |
| 3 | 434.42 | 435.86 |
| 4 | 421.28 | 41.4 |
| 5 | 400.86 | 15.88 |
| 6 | 402.45 | 75.3 |
| 7 | 358.44 | 125.7 |
| 8 | 377.27 | 406.38 |

Cellular Assays—Cell Growth Inhibition in PTEN-Deficient Cell Line MDA-MB-468

PTEN deficient tumor cell lines (MDA-MB-468) were cultured generally according to instructions supplied by cell culture supplier American Type Culture Collection, Manassas, Va., with 10% fetal bovine serum at 5% $CO_2$ and 37° C. Cells were seeded into either a T-75 or a T-175 flask 3-4 days prior to 96-well assay plating such that the flasks were approximately 70-80% confluent of the time of harvest. Cells were harvested using 0.25% trypsin-EDTA (Invitrogen #25200056). Trypan Blue exclusion staining was used to determine cell number.

Viable cells were plated in clear, flat bottom 96-well plates (BD #353075) under anchorage independent conditions at 2,000-10,000 cells per well depending on the cell line. To generate anchorage independent growth conditions, a 5% agar stock solution in water was made and autoclaved to melt and sterilize. From the 5% agar solution, a 0.6% agar/media+10% fetal bovine serum (FBS) solution was made to generate a bottom agar layer in the plates to prevent cell attachment. Seventy five microliters per well of the 0.6% agar-media solution was added to the plates. After solidification, a cell solution of 266,870 to 1,334,022 cells (depending on the cell line) in 10 ml of 0.3% agar/media+10% FBS was made and 75 μl of the cell/media/agar suspension was added to the plates. After the cell layer solidified, 50 μl of media+10% FBS was added to the top of the cells. A 0.3% Brij 35 (Sigma B4184) solution in media+10% FBS was added to column 12 as a background subtraction control. The cells were incubated overnight at 5% $CO_2$ and 37° C. The next day one plate of cells was processed at the time of compound addition to quantify the starting number of cells (T=0 or T0).

To generate the compound titration plates, 15 μl of a 2 mM or 20 μl of a 20 mM solution of the compound of example 31 was diluted in clear bottom polypropylene 96-well plate (BD #351190) using a 10 point, 3-fold titration or a 20 point 2-fold titration, respectively. Three hundred microliters of media was added to the compound dilutions. Ten microliters per well of the serial dilutions was added to the cells and the plates incubated for 6 days at 5% $CO_2$ and 37° C. The final concentration of DMSO in all wells was 0.15% and the highest final concentration of the compound of example 31 was 3.7 μM or 30.7 μM.

Following the 6-day incubation, 20 μl of Alamar Blue (Invitrogen #DAL1100) was added to the cells, incubated at 5% $CO_2$ and 37° C. for 6 hours and the plates read on a Spectramax (Gemini EM) at 530 nm (excitation) and 590 nm (emission) with the auto cut-off disabled. For analysis of cell growth inhibition dose response curves, the data was plotted as the percent of the DMSO-treated control samples (DMSO samples set to 100%). The cellular response was determined for compounds and control compounds by fitting the concentration response with a 4 parameter curve fit using XLfit software and determining the concentration that inhibits 50% of the Ymax-Ymin window ($EC_{50}$). The $EC_{50}$ is the midpoint of active compound effect window (between Ymax plateau and Ymin plateau of compound) and represents the concentration of the compound of example 31 where 50% of its maximal effect is observed. Values from wells containing 0.3% Brij 35 (under anchorage independent conditions) were subtracted from all samples for background correction. The compounds listed in Table 3 were tested generally according to the assays described herein. Table 3 lists the $EC_{50}$ values for either an experimental run or an average of two or more experimental runs with the examples shown.

TABLE 3

| Example # | MW | Prolif EC50 (nM) MDA-MB-468 |
|---|---|---|
| 3 | 434.42 | 41 |
| 4 | 421.28 | 152.8 |
| 5 | 400.86 | 18.1 |
| 6 | 402.45 | 66.5 |
| 8 | 377.27 | 1499 |

Additional References:

The compounds of the present invention can also be tested to determine their inhibitory activity at PI3Kα, PI3Kδ, PI3Kβ and PI3Kγ according to international patent publication No. WO2009/039140.

The pharmaceutically active compounds within the scope of this invention are useful as PI3 Kinase inhibitors in mammals, particularly humans, in need thereof.

The present invention therefore provides a method of treating diseases associated with PI3 kinase inhibition, particularly: autoimmune disorders, inflammatory diseases, cardiovascular diseases, neurodegenerative diseases, allergy, asthma, pancreatitis, multiorgan failure, kidney diseases, platelet aggregation, cancer, sperm motility, transplantation rejection, graft rejection and lung injuries and other conditions requiring PI3 kinase modulation/inhibition, which comprises administering an effective compound of Formula (I) or a pharmaceutically acceptable salt, hydrate, solvate or prodrug thereof. The compounds of Formula (I) also provide for a method of treating the above indicated disease states because of their ability to act as PI3 inhibitors. The drug may be administered to a patient in need thereof by any conventional route of administration, including, but not limited to, intravenous, intramuscular, oral, subcutaneous, intradermal, and parenteral.

Exemplary Capsule Composition

An oral dosage form for administering the present invention is produced by filing a standard two piece hard gelatin capsule with the ingredients in the proportions shown in Table 3, below.

TABLE 3

| INGREDIENTS | AMOUNTS |
|---|---|
| Compound of example 1 | 25 mg |
| Lactose | 55 mg |
| Talc | 16 mg |
| Magnesium Stearate | 4 mg |

Exemplary Injectable Parenteral Composition

An injectable form for administering the present invention is produced by stirring 1.5% by weight of compound of example 1 in 10% by volume propylene glycol in water.

Exemplary Tablet Composition

The sucrose, calcium sulfate dihydrate and an PI3K inhibitor as shown in Table 4 below, are mixed and granulated in the proportions shown with a 10% gelatin solution. The wet granules are screened, dried, mixed with the starch, talc and stearic acid; screened and compressed into a tablet.

TABLE 4

| INGREDIENTS | AMOUNTS |
|---|---|
| Compound of example 1 | 20 mg |
| calcium sulfate dehydrate | 30 mg |
| Sucrose | 4 mg |
| Starch | 2 mg |
| Talc | 1 mg |
| stearic acid | 0.5 mg |

While the preferred embodiments of the invention are illustrated by the above, it is to be understood that the invention is not limited to the precise instructions herein disclosed and that the right to all modifications coming within the scope of the following claims is reserved.

What is claimed is:

1. A compound of formula (I):

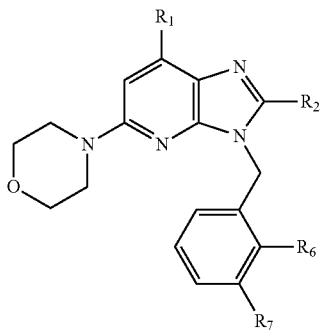

(I)

wherein
R1 is selected from H, —OH, and —C(O)OH;
R2 is selected from H, and $C_{1-3}$alkyl; and
each of R6 and R7 is independently selected from $C_{1-3}$alkyl, halogen, and —CF$_3$, or R6 and R7 combine with the ring to which they are attached to form napthtal;
or a pharmaceutically acceptable salt thereof.

2. The compounds of claim 1, having the formula (I)(A)

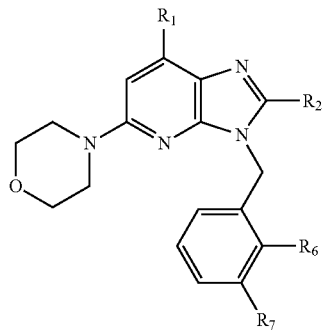

(I)(A)

wherein
R1 is selected from H, —OH, and —C(O)OH;
R2 is selected from H, and $C_{1-3}$alkyl; and
each of R6 and R7 is independently selected from $C_{1-3}$alkyl, halogen, and —CF$_3$;
or a pharmaceutically acceptable salt thereof.

3. The compounds of claim 1, having the formula (I)(B)

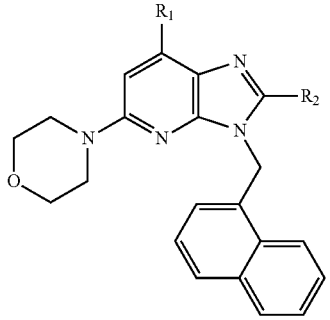

(I)(B)

wherein
R1 is selected from H, —OH, and —C(O)OH; and
R2 is selected from H, and $C_{1-4}$alkyl;
or a pharmaceutically acceptable salt thereof.

4. A compound selected from
3-(2-methyl-3-(trifluoromethyl)benzyl)-5-morpholino-3H-imidazo[4,5-b]pyridin-7-al;
5-morpholino-3-(naphthalen-1-ylmethyl)-3H-imidazo[4,5-b]pyridin-7-ol;
2-methyl-3-(2-methyl-3-(trifluoromethyl)benzyl)-5-morpholino-3H-imidazo[4,5-b]pyridine-7-carboxylic acid;
3-(2,3-dichlorobenzyl)-2-methyl-5-morpholino-3H-imidazo[4,5-b]pyridine-7-carboxylic acid;
3-(3-chloro-2-methylbenzyl)-2-methyl-5-morpholino-3H-imidazo[4,5-b]pyridine-7-carboxylic acid;
2-methyl-5-morpholino-3-(naphthalen-1-ylmethyl)-3H-imidazo[4,5-b]pyridine-7-carboxylic acid;
4-(2-methyl-3-(naphthalen-1-ylmethyl)-3H-imidazo[4,5-b]pyridin-5-yl)morpholine; and
4-(3-(2,3-dichlorobenzyl)-2-methyl-3H-imidazo[4,5-b]pyridin-5-yl)morpholine,
or a pharmaceutically acceptable salt thereof.

5. A method for treating a susceptible neoplasm in a mammal in need thereof, said method comprising administering to the mammal a therapeutically effective amount of a compound according to claim 1, wherein said susceptible neoplasm is a PTEN-deficient neoplasm selected from brain (gliomas), glioblastomas, leukemias, Bannayan-Zonana syndrome, Cowden disease, Lhermitte-Duclos disease, breast cancer, inflammatory breast cancer, colorectal cancer, Wilm's tumor, Ewing's sarcoma, Rhabdomyosarcoma, ependymoma, medulloblastoma, colon cancer, head and neck cancer, kidney cancer, lung cancer, liver cancer, melanoma, squamous cell carcinoma, ovarian cancer, pancreatic cancer, prostate cancer, sarcoma cancer, osteosarcoma, giant cell tumor of bone, thyroid cancer, lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, Plasmacytoma, Immunoblastic large cell leukemia, Mantle cell leukemia, Megakaryoblastic leukemia, multiple myeloma, Acute megakaryocytic leukemia, promyelocytic leukemia, Erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor), and testicular cancer.

6. The method according to claim 5, wherein said PTEN-deficient neoplasm is selected from hormone refractory prostate cancer, non-small-cell lung cancer, endometrial cancer, gastric cancer, melanoma, head and neck cancer, breast cancer, including trip-negative breast cancer, and glioma.

7. The method according to claim 5, wherein said mammal is a human.

* * * * *